(12) United States Patent
Aimone et al.

(10) Patent No.: US 11,520,404 B2
(45) Date of Patent: *Dec. 6, 2022

(54) WEARABLE COMPUTING DEVICE WITH ELECTROPHYSIOLOGICAL SENSORS

(71) Applicant: INTERAXON INC., Toronto (CA)

(72) Inventors: Christopher Allen Aimone, Scarborough (CA); Samuel Thomas MacKenzie, Toronto (CA); Graeme Daniel Moffat, Toronto (CA); Hubert Jacob Banville, Toronto (CA); Nicole Hélène Proulx, Toronto (CA)

(73) Assignee: INTERAXON INC., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/188,148

(22) Filed: Mar. 1, 2021

(65) Prior Publication Data

US 2021/0200313 A1 Jul. 1, 2021

Related U.S. Application Data

(63) Continuation of application No. 16/570,320, filed on Sep. 13, 2019, now Pat. No. 10,942,568, which is a
(Continued)

(51) Int. Cl.
*G09G 5/00* (2006.01)
*G06F 3/01* (2006.01)
(Continued)

(52) U.S. Cl.
CPC ............. *G06F 3/015* (2013.01); *A61B 5/369* (2021.01); *A61B 5/378* (2021.01); *A61B 5/6803* (2013.01);
(Continued)

(58) Field of Classification Search
CPC .......... G06F 1/163; G06F 3/011; G06F 3/015; G06F 3/016; G06F 3/04817; G06F 3/147;
(Continued)

(56) References Cited

U.S. PATENT DOCUMENTS 3,411,495 A * 11/1968 Casby .................. A61B 5/6814
600/383
4,084,583 A * 4/1978 Hjort ...................... A61B 5/291
600/544

(Continued)

FOREIGN PATENT DOCUMENTS

CN 205795690 U 12/2016

OTHER PUBLICATIONS

Supplementary European Search Report issued in Euopran Application No. EP 18809713, dated Feb. 2, 2021.
(Continued)

*Primary Examiner* — Joe H Cheng
(74) *Attorney, Agent, or Firm* — Norton Rose Fulbright Canada LLP

(57) ABSTRACT

A wearable computing device with bio-signal sensors and a feedback module provides an interactive mediated reality ("VR") environment for a user. The bio-signal sensors receive bio-signal data (for example, brainwaves) from the user and include bio-signal sensors embedded in a display isolator, having a deformable surface, and having an electrode extendable to contact the user's skin. The wearable computing device further includes a processor to: present content in the VR environment via the feedback module; receive bio-signal data of the user from the bio-signal sensor; process the bio-signal data to determine user states of the user, including brain states, using a user profile; modify a parameter of the content in the VR environment in response to the user states of the user. The user receives
(Continued)

feedback indicating the modification of the content via the feedback module.

20 Claims, 19 Drawing Sheets

Related U.S. Application Data continuation of application No. 15/993,275, filed on May 30, 2018, now Pat. No. 10,452,144.

(60) Provisional application No. 62/613,492, filed on Jan. 4, 2018, provisional application No. 62/512,555, filed on May 30, 2017.

(51) Int. Cl.
| | |
|---|---|
| *G09G 5/36* | (2006.01) |
| *G06F 1/16* | (2006.01) |
| *G06F 3/147* | (2006.01) |
| *A61B 5/00* | (2006.01) |
| *A61B 5/369* | (2021.01) |
| *A61B 5/378* | (2021.01) |
| *A61B 5/1455* | (2006.01) |
| *A61B 5/398* | (2021.01) |

(52) U.S. Cl.
CPC .............. *G06F 1/163* (2013.01); *G06F 3/011* (2013.01); *G06F 3/016* (2013.01); *G06F 3/147* (2013.01); *G09G 5/363* (2013.01); *A61B 5/0075* (2013.01); *A61B 5/14553* (2013.01); *A61B 5/398* (2021.01); *A61B 5/7264* (2013.01); *A61B 5/744* (2013.01); *A61B 2503/12* (2013.01); *G09G 2354/00* (2013.01); *G09G 2380/08* (2013.01)

(58) Field of Classification Search
CPC ....... A61B 5/0075; A61B 5/369; A61B 5/378; A61B 5/398; A61B 5/744; A61B 5/6803; A61B 5/7264; A61B 5/14553; A61B 2503/12; G09G 5/363; G09G 2354/00; G09G 2380/08
See application file for complete search history.

(56) References Cited

U.S. PATENT DOCUMENTS

| | | | |
|---|---|---|---|
| 4,355,912 A | | 10/1982 | Haak |
| 4,967,038 A | * | 10/1990 | Gevins ................ A61B 5/6814 600/383 |
| 9,398,864 B2 | | 7/2016 | Lawrence et al. |
| 9,622,703 B2 | * | 4/2017 | Badower ................ A61B 5/291 |
| 9,807,130 B2 | * | 10/2017 | Blattner ................ H04L 51/04 |
| 9,907,482 B2 | * | 3/2018 | Knight ................ A61B 5/0006 |
| 10,090,644 B2 | * | 10/2018 | Raring ............. H01S 5/320275 |
| 10,120,413 B2 | * | 11/2018 | Aimone ................ A61B 5/486 |
| 10,452,144 B2 | * | 10/2019 | Aimone .................. G06F 3/015 |
| 10,942,568 B2 | * | 3/2021 | Aimone .................. G06F 3/016 |
| 2002/0177767 A1 | | 11/2002 | Burton et al. |
| 2007/0225585 A1 | * | 9/2007 | Washbon ............. A61B 5/6803 600/393 |
| 2008/0027345 A1 | * | 1/2008 | Kumada ................ A61B 5/291 600/383 |
| 2009/0100351 A1 | * | 4/2009 | Bromenshenkel ........ G06F 3/01 715/757 |
| 2009/0214060 A1 | | 8/2009 | Chuang et al. |
| 2010/0198042 A1 | * | 8/2010 | Popescu ................. A61B 5/291 600/383 |
| 2012/0226127 A1 | * | 9/2012 | Asjes ..................... A61B 5/282 600/383 |
| 2013/0274583 A1 | | 10/2013 | Heck |
| 2013/0317382 A1 | * | 11/2013 | Le ........................... A61B 5/24 600/544 |
| 2014/0223462 A1 | * | 8/2014 | Aimone ............. H04N 21/4307 725/10 |
| 2014/0347265 A1 | * | 11/2014 | Aimone ................. H04W 4/029 345/156 |
| 2014/0354534 A1 | | 12/2014 | Mullins |
| 2015/0199010 A1 | | 7/2015 | Coleman et al. |
| 2016/0015289 A1 | * | 1/2016 | Simon .................. A61B 5/7275 600/301 |
| 2016/0077547 A1 | * | 3/2016 | Aimone ............... A61B 5/0022 345/8 |
| 2016/0262704 A1 | * | 9/2016 | Min ..................... A61B 5/0245 |
| 2016/0367189 A1 | * | 12/2016 | Aimone ................ A61B 5/291 |
| 2017/0209786 A1 | * | 7/2017 | Zhu .......................... A63F 13/92 |
| 2018/0286007 A1 | * | 10/2018 | Poornachandran ....... G06T 1/20 |

OTHER PUBLICATIONS

International Search Report and Written Opinion issued in International Application No. PCT/CA2018/050638, dated Aug. 7, 2018.

Stoppa, M. et al., "Wearable Electronics and Smart Textiles: A Critical Review", Sensors, vol. 14, Issue 7, p. 11957-11992, Jul. 7, 2014.

* cited by examiner

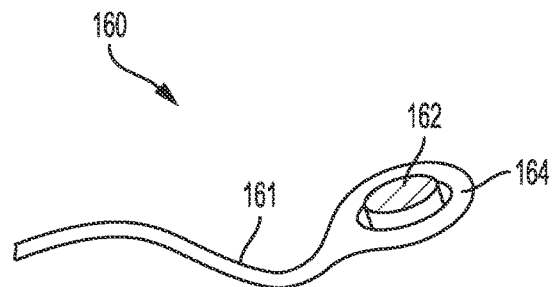
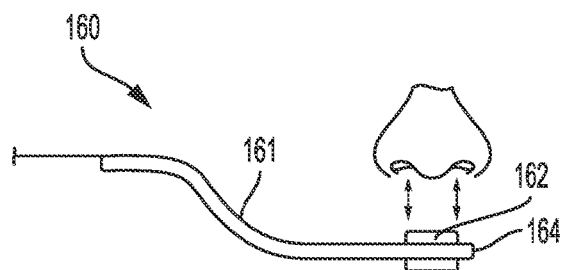
FIG. 25A
FIG. 25B
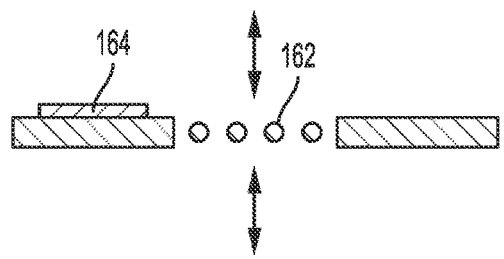
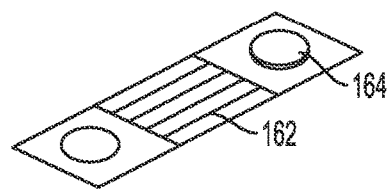
FIG. 26A
FIG. 26B
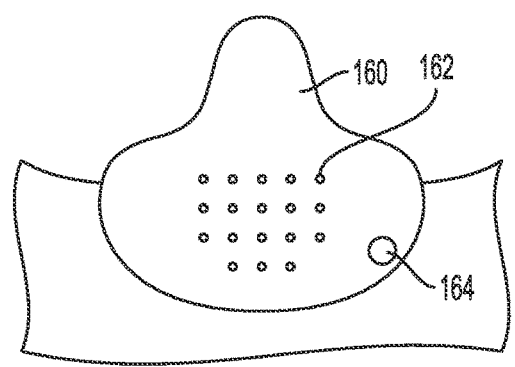
FIG. 27

WEARABLE COMPUTING DEVICE WITH ELECTROPHYSIOLOGICAL SENSORS

CROSS-REFERENCE TO RELATED APPLICATIONS

This application is a continuation of U.S. patent application Ser. No. 16/570,320, filed on Sep. 13, 2019, now U.S. Pat. No. 10,942,568 B2, which is a continuation of U.S. patent application Ser. No. 15/993,275, filed on May 30, 2018, now U.S. Pat. No. 10,452,144 B2, and claims benefit and priority from U.S. Provisional Patent Application No. 62/512,555 filed on May 30, 2017, and U.S. Provisional Patent Application No. 62/613,492 filed on Jan. 4, 2018, the contents of each of which are hereby incorporated by reference.

FIELD

The present invention relates to wearable devices. This invention relates more particularly to sensors for wearable devices and wearable devices with brain sensors. Even more particularly, this invention relates to wearable devices with brain sensors and methods for use in mediated reality environments.

BACKGROUND

A user may interact with a computing device for example using a keyboard, mouse, track pad, touch screen, or motion-capture devices. As the ways in which humans interact with computing devices change, computers may become usable for new purposes, or more efficient in performing existing tasks. A user command to a computing device that may require several commands on a keyboard may be instead associated with a single hand gesture captured and processed by a motion-capture input device. As the human body has many parts which may be controlled through voluntary movement, there are opportunities for capturing and interpreting other movements for interacting with a computing device.

Bio-signals are signals that are generated by biological beings that can be measured and monitored. Electroencephalographs, galvanometers, and electrocardiographs are examples of devices that are used to measure and monitor bio-signals generated by humans.

A human brain generates bio-signals such as electrical patterns, which may be measured/monitored using an electroencephalogram ("EEG"). These electrical patterns, or brainwaves, are measurable by devices such as an EEG. Typically, an EEG will measure brainwaves in an analog form. Then, these brainwaves may be analyzed either in their original analog form or in a digital form after an analog to digital conversion.

Measuring and analyzing bio-signals such as brainwave patterns can have a variety of practical applications. For example, brain computer interfaces ("BCI") allow users to control devices and computers using brainwave signals.

SUMMARY

In accordance with an aspect of the present invention, there is provided a mediated reality device comprising: an input device and a wearable computing device with a bio-signal sensor, a display to provide an interactive mediated reality environment for a user, and a display isolator, the bio-signal sensor receives bio-signal data from the user, the bio-signal sensor comprising a brainwave sensor, wherein the bio-signal sensor is embedded in the display isolator, wherein the bio-signal sensor includes a soft, deformable user-contacting surface.

In accordance with an aspect of the present invention, there is provided a mediated reality device comprising: an input device and a wearable computing device with a bio-signal sensor, at least one feedback module to provide an interactive mediated reality environment for a user, and a contact adjuster for adjusting contact between the bio-signal sensor and the user, the bio-signal sensor receives bio-signal data from the user, the bio-signal sensor comprising a brainwave sensor.

In accordance with an aspect of the present invention, there is provided a mediated reality device comprising: an input device and a wearable computing device with a bio-signal sensor, at least one feedback module to provide an interactive mediated reality environment for a user, and a conduction medium applicator for applying a conduction medium to a user contacting surface of the bio-signal sensor, the bio-signal sensor receives bio-signal data from the user, the bio-signal sensor comprising a brainwave sensor.

In accordance with an aspect of the present invention, there is provided a mediated reality device comprising: an input device and a wearable computing device with a bio-signal sensor, at least one feedback module to provide an interactive mediated reality environment for a user, and a conduction medium applicator for applying a conduction medium to a user contacting surface of the bio-signal sensor, the bio-signal sensor receives bio-signal data from the user, the bio-signal sensor comprising a brainwave sensor; the computing device having or in communication with a processor configured to: as part of the interactive mediated reality environment, present content via the at least one feedback module; receive user manual inputs from the input device for creating an object in the interactive mediated reality environment; receive the bio-signal data of the user from the bio-signal sensor, process the bio-signal data to determine user states of the user, including brain states, the user states are processed using a user profile stored in a data storage device accessible by the processor and the user states include brain states; modifying a property of the object according to the bio-signal data of the user.

In accordance with an aspect of the present invention, there is provided a mediated reality apparatus comprising: a wearable computing device with a bio-signal sensor and at least one feedback module to provide an interactive mediated reality ("VR") environment for a user, the bio-signal sensor receives bio-signal data from the user, the bio-signal sensor comprising a brainwave sensor; the computing device having or in communication with a processor configured to: as part of the interactive VR environment, present content via the at least one feedback module, the content including an object in the VR environment; receive the bio-signal data of the user from the bio-signal sensor; process the bio-signal data to determine user states of the user, including brain states, the user states are processed using a user profile stored in a data storage device accessible by the processor and the user states including brain states; modify a parameter of the object in the interactive VR environment in response to the user states of the user, wherein the user receives feedback indicating the modification of the object via the at least one feedback module.

In some embodiments, the processor is further configured to detect the user's interest in the object, and the parameter of the object is modified in response to the user's interest.

In some embodiments, the processor is configured to connect with a remote feedback device for presenting an indication of the user's interest to an observer.

In some embodiments, another object in the VR environment is created, modified, or both in response to the user's interest in the object. In some embodiments, the other object is an avatar of the user.

In some embodiments, the user profile includes a threshold for detection of a virtual event presented to the user by the at least one feedback module determined using the bio-signal data obtained concurrently with previous virtual events presented to the user. In some embodiments, the threshold for detection is modified based on the bio-signal data obtained during the presentation of the virtual event. In some embodiments, the content being presented in the VR environment is modified based on the threshold for detection for optimizing user engagement.

In some embodiments, the mediated reality apparatus includes a tracker for detecting the user's physical environment and the content of the VR environment is modified based on properties of the physical environment.

In some embodiments, the processor communicates with effectors in the user's physical environment for modifying the physical environment.

In accordance with an aspect of the embodiments described herein, there is provided a bio-signal sensor including a body, an electrode extendable into the body, the electrode having a contact end configured to receive an electrical bio-signal from a user's skin, wherein in response to a downward force acting on the bio-signal sensor to urge the bio-signal sensor against the user's skin and upon contact with the user's skin, the electrode is configured for movement into the body along a movement axis, an actuator attached to the body and operatively connected to the electrode urging the electrode out of the body along the movement axis toward an extended position, wherein in the absence of the downward force, the electrode is disposed in the extended position, and a contact adjuster connected to the electrode, the contact adjuster includes a handle manipulatable by the user to reduce noise the electrical bio-signal caused by impedance of the user's hair.

According to an aspect, there is provided a mediated reality device comprising: a wearable computing device with a bio-signal sensor to receive bio-signal data from a user, a display to provide an interactive mediated reality environment for the user, and a display isolator, the bio-signal sensor comprising a brainwave sensor, wherein the bio-signal sensor is embedded in the display isolator, the bio-signal sensor having a soft, deformable user-contacting surface.

In some embodiments, the bio-signal sensor comprises a conductive coating.

In some embodiments, the conductive coating comprises conductive ink.

In some embodiments, the mediated reality device further comprises a plurality of bio-signal sensors distributed along the display isolator and spaced to minimize salt bridging effects.

In some embodiments, the mediated reality device further comprises an optical device mounted on the display isolator.

In some embodiments, the bio-signal sensor comprises a cell for conductive fluid.

In some embodiments, the mediated reality device further comprises a conductive fluid reservoir in fluid connection with the cell for supplying the conductive fluid.

In some embodiments, the display isolator comprises a sensor to measure face movement or expression.

In some embodiments, the mediated reality device further comprises an eye tracker for gaze tracking.

In some embodiments, the mediated reality device further comprises a breath sensor attached to a deformable armature.

In some embodiments, the mediated reality device further comprises an ear piece having an additional bio-signal sensor.

In some embodiments, the mediated reality device further comprises a contact adjuster for adjusting contact between the bio-signal sensor and the user, In some embodiments, the mediated reality device further comprises at least one feedback module to update the interactive mediated reality environment for a user based on bio-signal data from the user received at the bio-signal sensor.

In some embodiments, the computing device is in communication with a processor configured to: as part of the interactive mediated reality environment, present content via the at least one feedback module; receive user manual inputs from the input device for creating an object in the interactive mediated reality environment; receive the bio-signal data of the user from the bio-signal sensor process the bio-signal data to determine user states of the user, including brain states, the user states processed using a user profile stored in a data storage device accessible by the processor and the user states including brain states; modify a property of the object according to the bio-signal data of the user to update the interactive mediated reality environment.

According to an aspect, there is provided a mediated reality device comprising: a wearable computing device with a bio-signal sensor, at least one feedback module to provide an interactive mediated reality environment for a user, and a contact adjuster for adjusting contact between the bio-signal sensor and the user, the bio-signal sensor receives bio-signal data from the user, the bio-signal sensor comprising a brainwave sensor.

In some embodiments, the computing device is in communication with a processor configured to: as part of the interactive mediated reality environment, present content via the at least one feedback module; receive user manual inputs from the input device for creating an object in the interactive mediated reality environment; receive the bio-signal data of the user from the bio-signal sensor; process the bio-signal data to determine user states of the user, including brain states, the user states processed using a user profile stored in a data storage device accessible by the processor and the user states including brain states; modify a property of the object according to the bio-signal data of the user to update the interactive mediated reality environment.

According to an aspect, there is provided a mediated reality device comprising: an input device and a wearable computing device with a bio-signal sensor to receive bio-signal data from a user, at least one feedback module to provide an interactive mediated reality environment for the user, and a conduction medium applicator for applying a conduction medium to a user contacting surface of the bio-signal sensor, the bio-signal sensor comprising a brainwave sensor.

In some embodiments, the computing device is in communication with a processor configured to: as part of the interactive mediated reality environment, present content via the at least one feedback module; receive user manual inputs from the input device for creating an object in the interactive mediated reality environment; receive the bio-signal data of the user from the bio-signal sensor process the bio-signal data to determine user states of the user, including brain states, the user states processed using a user profile stored in a data storage device accessible by the processor and the user states including brain states; modify a property of the object according to the bio-signal data of the user to update the interactive mediated reality environment.

In some embodiments, the mediated reality device further comprises a strap integrating the bio-signal sensor.

In some embodiments, the mediated reality device further comprises a display isolator, wherein the bio-signal sensor is embedded in the display isolator, wherein the bio-signal sensor has a soft, deformable user-contacting surface.

According to an aspect, there is provided a mediated reality apparatus comprising: a wearable computing device with a bio-signal sensor, to receive bio-signal data from a user, and at least one feedback module to provide an interactive mediated reality ("VR") environment for the user, the bio-signal sensor comprising a brainwave sensor; the computing device in communication with a processor configured to: as part of the interactive VR environment, present content via the at least one feedback module, the content including an object in the VR environment; receive the bio-signal data of the user from the bio-signal sensor; process the bio-signal data to determine user states of the user, including brain states, the user states processed using a user profile stored in a data storage device accessible by the processor and the user states including brain states; modify a parameter of the object in the interactive VR environment in response to the user states of the user, wherein the user receives feedback indicating the modification of the object via the at least one feedback module.

In some embodiments, the wearable computing device comprises the processor.

In some embodiments, the processor is configured to: detect the user's interest in the object, and modify the parameter of the object in response to the user's interest.

In some embodiments, the wearable computing device comprises a display isolator, wherein the bio-signal sensor is embedded in the display isolator, wherein the bio-signal sensor has a soft, deformable user-contacting surface.

In some embodiments, the processor is configured to: connect with a remote feedback device for presenting an indication of the user's interest to an observer.

In some embodiments, the processor is configured to: create and/or modify another object in the VR environment in response to the user's interest in the object.

In some embodiments, the other object is an avatar of the user.

In some embodiments, the user profile includes a threshold for detection of a virtual event presented to the user by the at least one feedback module determined using the bio-signal data obtained concurrently with previous virtual events presented to the user.

In some embodiments, the threshold for detection is modified based on the bio-signal data obtained during the presentation of the virtual event.

In some embodiments, the processor is configured to modify the content being presented in the VR environment based on the threshold for detection for optimizing user engagement.

In some embodiments, the mediated reality apparatus includes a tracker for detecting the user's physical environment and the processor is configured to modify the content of the VR environment based on properties of the physical environment.

In some embodiments, the processor communicates with effectors in the user's physical environment for modifying the physical environment.

In some embodiments, the bio-signal sensor comprises a capacitive electrode.

According to an aspect, there is provided a computer-implemented method comprising: receiving, from a bio-signal sensor, bio-signal data of a user of multiple users in a virtual or mixed environment; determining a transient electroencephalogram response of the user, based on at least the bio-signal data; detecting, based at least in part on the transient electroencephalogram response, the user's notice or attendance to a change in a transient or moving stimulus in the user's visual or auditory field in the virtual or mixed environment, and of characteristics of that stimulus encoded by the timecourse of the change; signalling to an outside observer that the user noticed or attended to the stimulus; signalling, to another observer in the virtual or mixed environment, that the user noticed or attended to the stimulus; and signalling, via an event in the virtual or mixed environment, which of the multiple users in said virtual or mixed reality environment noticed or attended to the stimulus.

In some embodiments, the signalling to another observer is effected via a change of facial expression on a virtual or holographic avatar, or a colour change of said avatar.

In some embodiments, the method further comprises measuring, using input of electrodes on the user's face or forehead, muscle activity associated with a facial expression of emotion; combining the user's brainwaves with bio-signal information about the facial expression; and producing a change in state of the user's avatar in said virtual or mixed environment based at least in part on the combined user's brainwaves and bio-signal information.

In some embodiments, the method further comprises: detecting diminution of the user's evoked brain response to a visual or auditory event in the virtual or environment after repeated stimulus presentations to predict how frequently a new stimulus of a certain type should be presented to the user to achieve familiarity.

In some embodiments, the method further comprises: detecting diminution of the user's evoked brain response to a visual or auditory event in the virtual or mixed environment after repeated stimulus presentations to predict how frequently a new stimulus of a certain type should be presented to the user to maintain a specific state of vigilance or responsiveness, or of interest.

According to an aspect, there is provided a mediated reality device comprising: a wearable computing device with a bio-signal sensor, at least one feedback module to provide an interactive mediated reality environment for a user, the bio-signal sensor receives bio-signal data from the user, the bio-signal sensor comprising a brainwave sensor, wherein the bio-signal sensor comprises: a body, an electrode extendable into the body, the electrode having a contact end configured to receive an electrical bio-signal from a user's skin, wherein in response to a downward force acting on the bio-signal sensor to urge the bio-signal sensor against the user's skin and upon contact with the user's skin, the electrode is configured for movement into the body along a movement axis, an actuator attached to the body and operatively connected to the electrode urging the electrode out of the body along the movement axis toward an extended position, wherein in the absence of the downward force, the electrode is disposed in the extended position, and a contact adjuster connected to the electrode, the contact adjuster including a handle manipulatable by the user to reduce noise the electrical bio-signal caused by impedance of the user's hair; wherein the computing device is in communication with a processor configured to: as part of the interactive mediated reality environment, present content via the at least one feedback module; receive user manual inputs from the input device for creating an object in the interactive mediated reality environment; receive the bio-signal data of the user from the bio-signal sensor; process the bio-signal data to determine user states of the user, including brain states, the user states processed using a user profile stored in a data storage device accessible by the processor and the user states including brain states; modify a property of the object according to the bio-signal data of the user to update the interactive mediated reality environment.

In some embodiments, the contact adjuster is configured to rotate the electrode along a plane that is substantially perpendicular to the movement axis.

In some embodiments, the actuator includes a coil spring fixed on one end to the body and biased against the electrode on the other end, and wherein the contact adjuster includes a shaft extending through the compressive axis of the coil spring for translating rotational forces perpendicular to the movement direction from the handle to the electrode, translational forces along the movement direction from the handle to the electrode, or both.

In some embodiments, the mediated reality device further comprises a rotational limiter for limiting the rotational movement of the electrode.

In some embodiments, the contact end of the electrode includes a collection plate and a plurality of prongs extending from the collection plate, wherein each prong includes a distal tip for contacting the user's skin.

In some embodiments, the radius of the distal tip is about 0.5 mm.

In some embodiments, the plurality of prongs are arranged with a prong density of about 15 to about 40 prongs per square centimeter.

In some embodiments, the actuator includes a plurality of actuators corresponding to the plurality of prongs.

In some embodiments, the contact end of the electrode has an area of between about 1 cm$^2$ and about 3 cm$^2$.

In some embodiments, the extension of the electrode from the body in the extended position is adjustable using the contact adjuster.

In some embodiments, the body includes a conductive portion for receiving the electrical bio-signal from the electrode.

In some embodiments, the conductive portion includes a conductive coating.

In some embodiments, the conductive portion includes a conductive material integrated into the body.

In some embodiments, the conductive material is a carbon-loaded plastic.

In some embodiments, the body includes a spherical portion, and wherein the sensor further comprises a housing defining a joint portion configured to receive the spherical portion of the body such that the body is rotatable within the joint portion.

In some embodiments, the body includes a contact end, wherein the contact end includes at least one groove for receiving at least a portion of the user's hair therein.

According to an aspect, there is provided a bio-signal sensor comprising: a body, an electrode extendable into the body, the electrode having a contact end configured to receive an electrical bio-signal from a user's skin, wherein in response to a downward force acting on the bio-signal sensor to urge the bio-signal sensor against the user's skin and upon contact with the user's skin, the electrode is configured for movement into the body along a movement axis, an actuator attached to the body and operatively connected to the electrode urging the electrode out of the body along the movement axis toward an extended position, wherein in the absence of the downward force, the electrode is disposed in the extended position, and a contact adjuster connected to the electrode, the contact adjuster including a handle manipulatable by the user to reduce noise the electrical bio-signal caused by impedance of the user's hair.

In some embodiments, the contact adjuster is configured to rotate the electrode along a plane that is substantially perpendicular to the movement axis.

In some embodiments, the actuator includes a coil spring fixed on one end to the body and biased against the electrode on the other end, and wherein the contact adjuster includes a shaft extending through the compressive axis of the coil spring for translating rotational forces perpendicular to the movement direction from the handle to the electrode, translational forces along the movement direction from the handle to the electrode, or both.

In some embodiments, the bio-signal sensor further comprises a rotational limiter for limiting the rotational movement of the electrode.

In some embodiments, the contact end of the electrode includes a collection plate and a plurality of prongs extending from the collection plate, wherein each prong includes a distal tip for contacting the user's skin.

In some embodiments, the radius of the distal tip is about 0.5 mm.

In some embodiments, the plurality of prongs are arranged with a prong density of about 15 to about 40 prongs per square centimeter.

In some embodiments, the actuator includes a plurality of actuators corresponding to the plurality of prongs.

In some embodiments, the contact end of the electrode has an area of between about 1 cm$^2$ and about 3 cm$^2$.

In some embodiments, the extension of the electrode from the body in the extended position is adjustable using the contact adjuster.

In some embodiments, the body includes a conductive portion for receiving the electrical bio-signal from the electrode.

In some embodiments, the conductive portion includes a conductive coating.

In some embodiments, the conductive portion includes a conductive material integrated into the body.

In some embodiments, the conductive material is a carbon-loaded plastic.

In some embodiments, the body includes a spherical portion, and the sensor further comprises a housing defining a joint portion configured to receive the spherical portion of the body such that the body is rotatable within the joint portion.

In some embodiments, the body includes a contact end, wherein the contact end includes at least one groove for receiving at least a portion of the user's hair therein.

In this respect, before explaining any embodiments described herein in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF DRAWINGS

Embodiments will now be described, by way of example only, with reference to the attached figures, wherein:

FIG. 25a illustrates a perspective view of a breath sensor, according to an embodiment;

FIG. 25b illustrates a schematic view of the breath sensor of FIG. 25a in use;

FIG. 26a illustrates a cross sectional view of a breath sensor, according to an embodiment;

FIG. 26b illustrates a perspective view of the breath sensor of FIG. 26a;

FIG. 27 illustrates a front view of a breath sensor, according to an embodiment;

Figure 1:
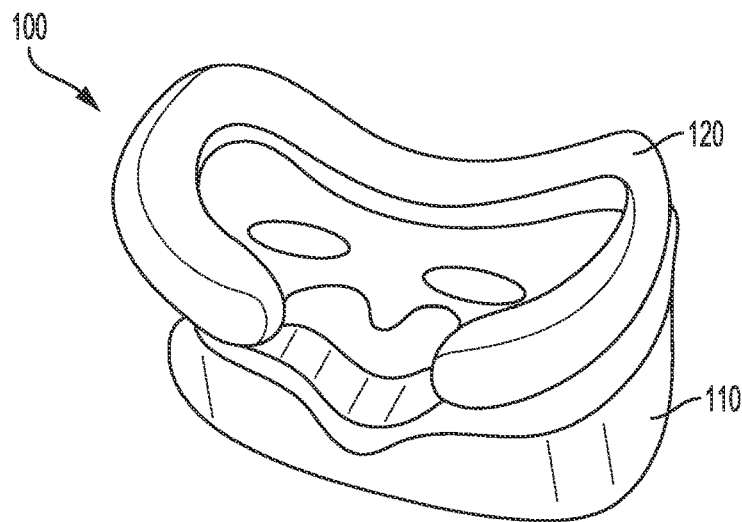
FIG. 1 illustrates a perspective view a wearable computing device, according to an embodiment.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

As used herein, the term "downward" refers to a direction toward a user's skin. Similarly, "lower" indicates a component disposed downward relative to another component. In contrast "upward" or "upper" are in a direction opposite the "downward" or "lower" component.

In an aspect, there is provided a computer system that is implemented by one or more computing devices. The computing devices may include one or more client or server computers in communication with one another over a near-field, local, wireless, wired, or wide-area computer network, such as the Internet, and at least one of the computers is configured to receive signals from sensors worn by a user. In an implementation, the sensors include one more bio-signal sensors, such as electroencephalogram (EEG) sensors, galvanometer sensors, electrocardiograph sensors, heart rate sensors, eye-tracking sensors, blood pressure sensors, pedometers, gyroscopes, and any other type of sensor. The sensors may be of various types, including: electrical bio-signal sensor in electrical contact with the user's skin; capacitive bio-signal sensor in capacitive contact with the user's skin; blood flow sensor measuring properties of the user's blood flow; and wireless communication sensor placed sub-dermally underneath the user's skin. Other sensor types may be possible. The sensors may be connected to a wearable computing device, such as a wearable headset, wearable eyeglass frames, or headband computer worn by the user. The sensors may be connected to the headset by wires or wirelessly. The headset may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud-based or software as a service platform (SAAS) servers. Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable computing device), external sensors (contained outside the wearable computing device), user effectors, and any servers may be encrypted. Collected and analyzed data may be used to build a user profile that is specific to a user. The user profile data may be analyzed, such as by machine learning algorithms, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable computing device or other local computing device for providing feedback to the user, for example, to vibrate or provide some audio or visual indication to assist the user in achieving a particular mental state, such as a meditative state.

The wearable computing device may include a camera, a display, and bio-signal measuring means to sample a user's environment as well as the user's bio-signals, determining the user's state and context through sensors and user input. The wearable computing device may include at least one user-facing camera to track eye movement. In a particular aspect of the invention, the wearable computing device may be in a form resembling eyeglasses wearable on the user's face. Optionally, at least one camera may be oriented to generally align with the user's field of view.

In another aspect of the invention, the wearable computing device includes at least one sensor adapted to being placed at or adhered to the user's head or face. Each sensor may optionally communicate with one another either through wires or wirelessly. Each sensor may optionally communicate with a controller device either through wires or wirelessly. The controller device may be mounted to the wearable computing device in order to reside at or near the user's head or face. Alternatively, the controller device may be located elsewhere on the user's body, such as in a bag or pocket of the user's clothing. The controller device may also be disposed somewhere outside the user's body. For example, the sensors may monitor the user, storing data in local storage mounted to the wearable computing device, and once moving into proximity with the controller device, the sensors, or a transmitter of the wearable computing device may transmit stored data to the controller device for processing. In this implementation, the wearable computing device would be predominantly usable by the user when located nearby the controller device.

The wearable computing device may include a camera, a display and bio-signal measuring means. At least one of the bio-signal measuring means may employ at least one sensor in order to measure brain activity. Brain activity may be measured through electroencephalography ("EEG") techniques electrically, or through functional near-infrared spectroscopy ("fNIRS") techniques measuring relative changes in hemoglobin concentration through the use of near infrared light attenuation. A sensor employing pulse oximetry techniques may also be employed in the wearable computing device. Optionally, the wearable computing device may include at least one sensor measuring eye activity using electrooculography ("EOG") techniques. Other sensors tracking other types of eye movement may also be employed.

In various implementations, the wearable computing device may include a variety of other sensors and input means. For example, the wearable computing device may comprise at least one audio transducer such as a single microphone, a microphone array, a speaker, and headphones. The wearable computing device may comprise at least one inertial sensor for measuring movement of the wearable computing device. The wearable computing device may comprise at least one touch sensor for receiving touch input from the user.

The wearable computing device may sample from both the user's environment and bio-signals simultaneously or generally contemporaneously to produce sampled data. The sampled data may be analyzed by the wearable computing device in real-time or at a future predetermined time when not being worn by the user.

The wearable computing device may comprise user input detection methods that are adaptive and improve with use over time. Where the user attempts to command the wearable computing device, and the wearable computing device responds in an unexpected way, the user may attempt to correct the previous input by indicating that the wearable computing device response was incorrect, and retrying the initial command again. Over time, the wearable computing device may refine its understanding of particular user inputs that are corrected. Some user inputs may be easier to successfully measure with a high degree of accuracy than others. It may be preferable to assign a high-accuracy input to command the wearable computing device that the previous input was incorrect. For example, tapping the wearable computing device in a particular spot may indicate that the previous input response was incorrect. Explicit training such as with voice recognition may also be used to configure and command the wearable computing device.

In one implementation, the wearable computing device may be in a glasses-like form factor. Glasses, with or without eyeglass elements, may be well-suited on which to mount sensors as glasses may be easily mounted to the user's face, and are easily removed. Glasses may also be relatively stable in position with respect to the user's head when resting on parts of the user's nose and ears. In order to further reduce movement of the glasses, arm-portions of the glasses may grip sides or rear portions of the user's head. Resilient arm-portions may be particularly useful for achieving a suitable gripping strength, thereby minimizing movement of the glasses and any sensors mounted thereupon.

Optionally, the wearable computing device may itself only provide bio-signal sensors and a processor for processing measurements from the sensors. The wearable computing device may communicate these measurements or data derived from processing the measurements to one or more secondary devices, such as a Google Glass-style device. In any of the implementations, embodiments, or applications discussed herein, it should be understood that some actions may be carried out by a plurality of interconnected devices, or just one of the wearable computing devices of the present invention. For example, the wearable computing device may not include a display. In such an example, the wearable computing device may communicate visual information to the user through the use of a second device, such as a Google Glass-style device, which does include a display.

Sensors usable with the wearable computing device may come in various shapes and be made of various materials. For example, the sensors may be made of a conductive material, including a conductive composite like rubber or conductive metal. The sensors may also be made of metal plated or coated materials such as stainless steel, silver-silver chloride, and other materials.

In addition to or instead of processing bio-signal measurements on the wearable computing device, the wearable computing device may communicate with one or more computing devices in order to distribute, enhance, or offload the processing of the bio-signal measurements taken or received by the wearable computing device. In particular, the one or more computing devices may maintain or have access to one or more databases maintaining bio-signal processing data, instructions, algorithms, associations, or any other information which may be used or leveraged in the processing of the bio-signal measurements obtained by the wearable computing device. The computing devices may include one or more client or server computers in communication with one another over a near-field, local, wireless, wired, or wide-area computer network, such as the Internet, and at least one of the computers may be configured to receive signals from sensors of the wearable computing device.

The wearable computing device may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud-based or software as a service platform (SAAS) servers. Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable computing device), external sensors (contained outside the wearable computing device), user effectors (components used to trigger a user response), and any servers may be encrypted. Collected and analyzed data may be used to build a user profile that is specific to a user. The user profile data may be analyzed, such as by machine learning algorithms, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable computing device or other local computing device for providing feedback to the user, for example, to vibrate or provide some audio or visual indication to assist the user in achieving a particular mental state, such as a meditative state.

A cloud-based implementation for processing and analyzing the sensor data may provide one or more advantages including: openness, flexibility, and extendibility; manageable centrally; reliability; scalability; being optimized for computing resources; having an ability to aggregate information across a number of users; and ability to connect across a number of users and find matching sub-groups of interest. While embodiments and implementations of the present invention may be discussed in particular non-limiting examples with respect to use of the cloud to implement aspects of the system platform, a local server, a single remote server, a SAAS platform, or any other computing device may be used instead of the cloud.

In one implementation of the system of the present invention, a Multi-modal EEG Data-Collection and Adaptive Signal Processing System (MED-CASP System) for enabling single or multi-user mobile brainwave applications may be provided for enabling BCI applications. This system platform may be implemented as a hardware and software solution that is comprised of an EEG headset such as the wearable computing device of the present invention, a client side application and a cloud service component. The client side application may be operating on a mobile or desktop computing device. The system may provide for estimation of hemispheric asymmetries and thus facilitate measurements of emotional valence (e.g. positive vs. negative emotions); and better signal-to-noise ratio (SNR) for global measurements and thus improved access to high-beta and gamma bands, which may be particularly important for analyzing cognitive tasks such as memory, learning, and perception. It has also been found that gamma bands are an important neural correlate of meditation expertise.

In the same or another non-limiting exemplary implementation, possible MED-CASP system features may include: uploading brainwaves and associated sensor and application state data to the cloud from mobile application; downloading brainwave & associated data from the cloud; real-time brain-state classification to enable BCI in games or other applications; transmitting real-time brain-state data to other users when playing a game to enable multi-user games; sharing brainwave data with other users to enable asynchronous comparisons of results; sharing brainwave data to other organizations or third party applications and systems; and support of cloud-based user profiles for storing personal information, settings and pipeline parameters that have been tuned to optimize a specific user's experience. In this way, usage of the system platform can be device independent.

Each time analysis or processing of user bio-signal data (such as brainwave data) is performed, an instance of aspects of the software implementing the analysis functionality of the present invention may be generated by the wearable computing device, initiated at either the device or the cloud, in order to analyze the user's private bio-signal data using particular analysis or processing parameters applied during the analysis or processing. For simplicity, such an instance may be referred to as an algorithm "pipeline". Each instance of the pipeline may have an associated pipeline identifier ("ID"). Each pipeline may be associated with a particular activity type, user, bio-signal type of a particular user, application, or any other system platform-related data. Each pipeline may maintain particular pipeline parameters determined to analyze the user's bio-signal data in a particular way, consistent either with previous analysis of the particular user's bio-signal data, consistent with previous analysis of one or more other user's bio-signal data, or consistent with updated data at the cloud server derived from new or updated scientific research pertaining to the analysis of bio-signal data. Pipelines and/or pipeline parameters may be saved for future use at the client computing device or at the cloud. When a new pipeline is created for the user, the wearable computing device or the cloud may provide a new algorithm pipeline ID to be associated with the new pipeline at the cloud and at the device.

Each person's brainwaves are different, therefore requiring slightly different tunings for each user. Each person's brain may also learn over time, requiring the system platform to change algorithm parameters over time in order to continue to analyze the person's brainwaves. New parameters may be calculated based on collected data, and may form part of a user's dynamic profile (which may be called bio-signal interaction profile). This profile may be stored in the cloud, allowing each user to maintain a single profile across multiple computing devices. Other features of the same or another non-limiting exemplary implementation may include: improving algorithms through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience). The core functionality of the MED-CASP system may be wrapped as an externally-usable library and API so that another developer may use the platform's features in the developer's application(s). The library may be a static library and API for Unity3D, iOS, Android, OSX, Windows, or any other operating system platform. The system platform may also be configured to use a pre-compiled algorithm supplied by a third party within the library, including the ability for a third party developer using the library, to use the developer's own algorithms with the library. The system platform may also support headsets from a variety of vendors; personal data security through encryption; and sharing of un-curated data (optionally using time-limited and fidelity limited access) through the sharing of encryption keys.

Optionally, the wearable computing device of the present invention may be used to implement aspects of the systems and methods described in PCT Patent Application No. PCT/CA2013/000785, filed Sep. 16, 2013, the entirety of which is incorporated by reference herein. Accordingly, the wearable computing device may be used with a computer network implemented system for improving the operation of one or more biofeedback computer systems. The system may include an intelligent bio-signal processing system that is operable to: capture bio-signal data and in addition optionally non-bio-signal data; and analyze the bio-signal data and non-bio-signal data, if any, so as to: extract one or more features related to at least one individual interacting with the biofeedback computer system; classify the individual based on the features by establishing one or more brainwave interaction profiles for the individual for improving the interaction of the individual with the one or more biofeedback computer systems, and initiate the storage of the brain wave interaction profiles to a database; and access one or more machine learning components or processes for further improving the interaction of the individual with the one or more biofeedback computer systems by updating automatically the brainwave interaction profiles based on detecting one or more defined interactions between the individual and the one or more of the biofeedback computer systems.

Optionally, the wearable computing device may be used to implement aspects of the systems and methods described in PCT Patent Application No. PCT/CA2013/001009, filed Dec. 4, 2013, the entirety of which is incorporated by reference herein. Accordingly, the wearable computing device may be used with a computer system or method for modulating content based on a person's brainwave data, obtained by the sensors of the wearable apparatus of the present invention, including modifying presentation of digital content at at least one computing device. The content may also be modulated based on a set of rules maintained by or accessible to the computer system. The content may also be modulated based on user input, including through receipt of a presentation control command that may be processed by the computer system of the present invention to modify presentation of content. Content may also be shared with associated brain state information.

Optionally, the wearable computing device may be used to implement aspects of the systems and methods described in PCT Patent Application No. PCT/CA2014/000004, filed Jan. 6, 2014 the entirety of which is incorporated by reference herein. Accordingly, the wearable computing device may be used with a computer system or method for guiding one or more users through a brain state guidance exercise or routine, such as a meditation exercise. The system may execute at least one brain state guidance routine comprising at least one brain state guidance objective; present at least one brain state guidance indication at the at least one computing device for presentation to at least one user, in accordance with the executed at least one brain state guidance routine; receive bio-signal data of the at least one user from the at least one bio-signal sensor, at least one of the at least one bio-signal sensor comprising at least one brainwave sensor, and the received bio-signal data comprising at least brainwave data of the at least one user; measure performance of the at least one user relative to at least one brain state guidance objective corresponding to the at least one brain state guidance routine at least partly by analyzing the received bio-signal data; and update the presented at least one brain state guidance indication based at least partly on the measured performance. The system may recognize, score, and reward states of meditation, thereby optionally gamifying the experience for the user. The system, using bio-signal data measurements measured by the wearable computing device, and in particular brainwave state measurements, may change the state of what is displayed on the display of the wearable computing device. For example, in response to a determination that the user has achieved a particular brain state, or maintained a particular brain state for a period of time, the wearable computing device may update the display to provide an indication of the determination (e.g. indicating to the user what brain state has been achieved, and, optionally for how long) and may further display an indication of a particular reward assigned to the user in response to the determination.

Optionally, the wearable computing device may be used to implement aspects of the systems and methods described in PCT Patent Application No. PCT/CA2014/000256, filed Mar. 17, 2014 the entirety of which is incorporated by reference herein. Accordingly, the wearable computing device may implement a method including: acquiring at least one bio-signal measurement from a user using the at least one bio-signal measuring sensor. The at least one bio-signal measurement may include at least one brainwave state measurement. The wearable computing device may process the at least one bio-signal measurement, including at least the at least one brainwave state measurement, in accordance with a profile associated with the user. The processing of the at least one bio-signal measurement includes filtering to remove line noise, transforming the signal to an alternate domain (e.g. using Fourier or Laplace transforms). The wearable computing device may determine a correspondence between the processed at least one bio-signal measurement and at least one predefined device control action. In accordance with the correspondence determination, the wearable computing device may control operation of at least one component of the wearable computing device. Various types of bio-signals, including brainwaves, may be measured and used to control the device in various ways. The controlling operation of at least one component of the wearable computing device may comprise sharing the processed at least one brainwave state measurement with at least one computing device over a communications network. Thresholds of brain state may be learned from each user.

Optionally, the wearable computing device may be used to implement aspects of the systems and methods described in U.S. patent application Ser. No. 14/851,853, filed Sep. 11, 2015, the entirety of which is incorporated by reference herein. In an aspect, the wearable computing device may implement a method including: as part of an interactive VR environment, present content on the display where the content has a VR event, desired user states, and desired effects; receive user manual inputs from an input device which have effects in the interactive VR environment including during the VR event; receive bio-signal data of a user from a bio-signal sensor during the VR event; process the bio-signal data to determine user states of the user, including brain states, during the VR event, the user states are processed suing a user profile stored in a data storage device accessible by the processor and the user states include brain states; determine a user state score by comparing the user states of the user to the desired user states during the course of the VR event; determine a performance score by comparing the user states of the user to the desired user states during the course of the VR event; and provide feedback to the user of the user wherein the feedback is based on a combination of the user states score and the performance score.

Optionally, the wearable computing device may be used to implement aspects of the systems and methods, for example, a method including: as part of an interactive VR environment, present content via at least one feedback module, the content including an object in the VR environment; receiving the bio-signal data of the user from a bio-signal sensor, processing the bio-signal data to determine user states of the user, including brain states, the user states processed using a user profile stored in a data storage device accessible by the a processor and the user states including the brain states, and modifying a parameter of the object in the interactive VR environment in response to the user states of the user, wherein the user receives feedback indicating the modification of the object via the at least one feedback module.

In accordance with an aspect of the present invention, there is provided a wearable computing device including at least one feedback module, and at least one bio-signal sensor. The wearable computing device includes or is in communication with a processor configured, as part of a mediated reality environment, to apply at least one stimulus to a user via the at least one feedback module.

In some embodiments, the at least one stimulus provided by the at least one feedback module affects a sensory modality including sight, sound, taste, temperature, smell, pressure or any combination thereof.

In some embodiments, stimuli from the physical, real-world environment of a user is supplemented by the at least one stimulus from the at least one feedback module. In such embodiments, the mediated reality environment is an augmented reality environment. In some embodiments, at least one type of stimuli from the physical, real-world environment of a user is replaced by the at least one stimulus from the at least one feedback module. In such embodiments, the mediated reality environment is a virtual reality environment. The term "VR environment", as used hereinafter, refers to mediated reality environments generally, and can include both virtual reality and augmented reality environments. A user may interact in the VR environment using input data such as gesture data, manual inputs, sensor data, bio-signal sensor data, and so on.

In some embodiments, the at least one stimulus modality includes sight and the at least one feedback module includes a display. In some embodiments, the display is a stereoscopic display for displaying the visual stimulus. The stereoscopic display optionally displays two 2-dimensional images, that when observed by a user, are interpreted as a single 3-dimensional image.

In some embodiments, the display is a head mounted display ("HMD"). In some embodiments, the HMD includes translucent and/or transparent portions such that the displayed information is a heads-up display. In some embodiments, the wearable computing device includes a front facing image sensor and an image obtained from the front facing image sensor is displayed on the HMD for creating a virtual heads-up display.

Optionally, the wearable computing device includes a display isolator for reducing or eliminating visual stimuli from sources other than the display. In some embodiments, the display isolator sits between the user's face and the display. In some embodiments, the display isolator is configured to contact the user's face. In some embodiments, the surface of the display isolator that rests on the user's face includes the at least one bio-signal sensor embedded thereon. In some embodiments, the portion of the display isolator that contacts the user's face includes a soft, deformable material. In some embodiments, the display isolator defines an aperture through which a user is able to view the display. In some embodiments, the display isolator is a mask. In some embodiments, the display isolator is a shroud.

In some embodiments, the wearable computing device applies an electrical signal for providing a feedback from the VR environment. The user may perceive the applied electrical signal as a tingle or shock depending on the voltage, current, and duration of the applied electrical signal. Further, the applied electrical signal may cause muscles to contract. In some embodiments, one or more of the bio-signal sensors are configured to apply the electrical signal such that the at least one feedback module includes the one or more bio-signal sensors. The bio-signal sensors can obtain bio-signal data from the user, but when a voltage is applied, can also apply the electrical signal. In some embodiments, the obtaining of the bio-signal data and the applying of the electrical signal occur in half-duplex mode or in full-duplex mode. In full-duplex mode, the applying of the electrical signal may occur concurrently with the obtaining of the bio-signal data. In full-duplex mode, the range of frequencies of the electrical signal being applied are different than the ranges frequencies of the bio-signal data being obtained. This reduces possible interference effects by the two signals. For example, the bio-signal data being obtained may have a frequency from above 0 to about 30 Hz while the applied electrical signal has a frequency of about 40 Hz or higher. In half-duplex mode, the bio-signal sensors alternate between applying the electrical signal and obtaining bio-signal data. The width of the pulses for applying the electrical signal and obtaining the bio-signal data is selected to minimize the gaps in obtaining the bio-signal. In some embodiments, the width of the pulses is between about 2 seconds and about 30 seconds. In some embodiments, the at least one feedback module is an electrical signal generator for applying the electrical signal. The electrical signal generator may be able to apply a larger voltage than the bio-signal sensors. In this manner, a larger stimulus may be applied.

In some embodiments, the at least one stimulus modality includes pressure and the at least one feedback modules includes a pressure transducer. In some embodiments, the mediated reality is able to actuate the pressure transducer such that the user is able to feel pressure, forces, vibrations or motions. In some embodiments, the pressure transducer provides haptic feedback for the user.

In some embodiments, the at least one stimulus modality includes sound and the at least one feedback modules includes a sound generator for providing audio stimulus to the user. In some embodiments, the sound generator includes two speaker drivers. One of the two speaker drivers may be placed proximate one ear of the user and the other of the two speaker drivers may be placed proximate the other ear of the user. The two speaker drivers may drive audio in stereo.

In some embodiments, the wearable computing device includes an ear-mounted portion, and the ear-mounted portion includes the sound generator. In some embodiments, the wearable computer device includes two ear-mounted portions, each including one or more speaker drivers. Each ear-mounted portion includes a circumaural pad. The circumaural pad rests around the ear of the user. In some embodiments, the circumaural pad includes ear-adjacent bio-signal sensors. In some embodiments, the ear-mounted portion includes in-ear electrodes. In-ear electrodes provide a similar signal to scalp electrodes, but may have increased signal-to-noise ratios as there may be less interference from EMG signals. In some embodiments, the at least one ear-mounted portion is detachable from the wearable computing device. In some embodiments, the ear-mounted portion includes a connector for establishing a wired connection that complements a receiver on a securement strap portion of the wearable computing device.

In using the wearable computing device, the bio-signal sensors are required to be in electrical connection with the user's skin in order to obtain bio-signal data. Current methods of verifying that the electrical connection between the bio-signal sensors and the user's skin is established include obtaining signals from the bio-signal sensors. The inability to obtain bio-signal data from the bio-signal sensors, or noisy or weak bio-signal data indicates that the electrical connection is not established or is poor. However, such processes require time to collect and interpret the bio-signal data obtained from the sensors. In some embodiments, the bio-signal sensors output a connection signal. When the bio-signal sensors are in electrical connection with the user's skin, the connection signal is received by nerves on the user's skin and is perceived as a mild shock or tingle.

In order to obtain bio-signal data from a user, the bio-signal sensors may sit or be pressed against a user's skin. Current bio-signal sensors can include hard metallic electrodes. When worn for an extended time, the hard metallic electrodes pressed against their skin create pressure points, which a user may perceive as being uncomfortable. For example, when the metallic electrodes have small contact areas against the skin, the user may perceive such electrodes as being "prickly". In some embodiments, the bio-signal sensors include a soft, deformable material for distributing pressure applied by the bio-signal sensors. In some embodiments, the soft, deformable material includes a conductive coating. In some embodiments, the conductive coating includes silver, carbon, a conductive polymer, hydrogel, UV curable conductive hydrogel. In some embodiments, the conductive polymer includes poly(3,4-ethylenedioxythiophene) ("PEDOT"). In some embodiments the PEDOT is poly(3,4-ethylenedioxythiophene)polystyrene sulfonate (PEDOT:PSS).

The conductive coating may be applied to a bio-signal sensor by dipping, screen printing, inkjet printing, spraying, or pad printing. In some embodiments, the conductive coating includes a conductive ink including silver, graphite or both. For example, PE872 from El DuPont de Nemours is a silver-bearing composition that possess suitable stretchability, adhesion, and conductive properties that is compatible with polyurethane, like thermoplastic polyurethane (TPU), and synthetic fabrics. In some embodiments, the conductive coating includes PEDOT:PSS. For example, Clevious PH1000 from Haraeus, is an aqueous PEDOT:PSS suspension including adhesion, stretchability and conductivity additives. In some embodiments, the PEDOT:PSS composition includes application additives. The application additives include surfactants, plasticizers, matting agents, solvents, binders, or combinations thereof. For example, ionic additives to assist stretchability an electrical conductivity is discussed in Y. Wang, C. Zhu, R. Pfattner, H. Yan, L. Jin, S. Chen, F. Molina-Lopez, F. Lissel, J. Liu, N. I. Rabiah, Z. Chen, J. W. Chung, C. Under, M. F. Toney, B. Murmann, Z. Bao, A highly stretchable, transparent, and conductive polymer. Sci. Adv. 3, e1602076 (2017), which is hereby incorporated by reference.

In some embodiments, the bio-signal sensors include a conductive rubber. Conductive rubber includes conductivity additives incorporated therein. In some embodiments, bio-signal sensor include an injection molded conductive rubber. In some embodiments, the injection molded conductive rubber includes TPU, thermoplastic elastomer (TPE), thermoplastic vulcanizate (TPV), styrene ethylene butylene streyene (SEBS) (such as Lifoflex UV 60.01B03872F from HEXPOL TPE), or compression or injection silicones (such as ELASTOSIL@R570/60 from Wacker Chemie). In some embodiments, the conductivity additive includes silver particles, carbon particles, carbon nanotubes, silver fibers, stainless steel fibers, PEDOT:PSS, hydrogels, or combinations thereof. In some embodiments, the conductive rubber includes adhesion additives. For example, Kraton FG1901 G may be added to a SEBS rubber to increase polarity and improve coating adhesion.

In some embodiments, the bio-signal sensor includes conductive threads. Conductive threads may be thin, flexible and durable. However, certain conductive threads may have relatively high impedance. In some embodiments, the conductive threads are used in electrodes measuring impedance-tolerant bio-signals, such as EMG and EOG bio-signals, or where an operational amplifier is placed near the electrode, such as within one millimeter. In some embodiments, wiring of bio-sensors include conductive threads providing electrical conductivity between electrode regions and other electrical components. In some embodiments, the conductive thread is made entirely from metal. In some embodiments, the metallic conductive thread includes 316 stainless steel. For example, 316 stainless steel may be a thread spun from stainless steel fibers, such as a 8 micron fiber. In some embodiments, the metallic thread includes silver. In some embodiments, the metallic thread includes a polymer core coated or plated with a metal. In some embodiments, the polymer core includes polyamide. In some embodiments, the conductive thread includes a conductive coating, such as PEDOT:PSS.

In some embodiments, the bio-signal sensor includes a conductive fabric. The conductive fabric may be a stretchable or non-stretchable conductive fabric. In some embodiments, the conductive fabric includes woven conductive threads, optionally woven with non-conductive threads. In some embodiments, the conductive fabric includes woven non-conductive threads, optionally woven with conductive threads, and a conductive coating applied thereon.

In some embodiments, the bio-signal sensor includes a contact electrode. The contact electrode is an object or material that is in contact with the user's skin for the purpose of measuring electric potential or current flow. In some embodiments, the bio-signal sensor includes a non-contact electrode. The non-contact electrode is an object or material that is not in contact with the user's skin for measuring electric potential through capacitive coupling. Where skin contact is not easily achieved, for example, due to hair on a user's head, a capacitive non-contact electrode may have a better signal to noise ratio than a contact electrode making poor or no contact with the user's head.

In some embodiments, bio-signal sensor is attached to the user with a conductive adhesive. In some embodiments, the conductive adhesive includes conductive ink, two-component conductive epoxy, conductive pressure sensitive adhesive, conductive transfer tape, Z-directional conductive transfer tape.

In some embodiments, at least a portion of the bio-signal sensors are embedded in the display isolator. In some embodiments, the embedded bio-signal sensors are level with the portion of the display isolator that contacts the user's face. In some embodiments, a polymer coating is applied to the display isolator and/or the embedded bio-signal sensor to create a smooth surface. In some embodiments, the display isolator is a soft face pad or mask.

In some embodiments, the wearable computing device includes a contact adjuster for improving contact between bio-signal sensor and the user. The bio-signal sensors should be in contact with the skin in order to obtain accurate bio-signal data. Obstructions disposed between the bio-signal sensor and the skin may reduce the accuracy of the bio-signal data. For example, hair disposed between a bio-signal sensor and the scalp impedes the creation of an electrical connection between the bio-signal sensor and the scalp. Further, hair may form a "mat" that lifts the bio-signal sensor away from the skin, further impeding the creation of an electrical connection between the bio-signal sensor and the scalp. Current electrodes may be shaped like prongs to penetrate through a "mat" of hair. However, such prongs may be uncomfortable when worn. In some embodiments, the contact adjuster includes a fixation strap. The fixation strap applies tension against the user's head. In some embodiments, the tension applied by the fixation presses the bio-signal sensor against the skin, reducing the lift of a "mat" of hair. In some embodiments, the contact adjuster includes a sensor housing. The sensor housing includes a user contact surface and at least a portion of the bio-signal sensors. In some embodiments, the sensor housing includes a retracted position and an extended position. In the retracted position, the user contact surface is configured to contact the user and the bio-signal sensors are flush with the user contact surface (e.g. having surfaces in the same or similar plane, even) or are offset such that the bio-signal sensors are not in contact with the user. In the extended position, the bio-signal sensors protrude from the user contact surface for contacting the user's skin. In some embodiments, the sensor housing defines channels through which the bio-signal sensors retract and extend. In some embodiments, a biasing member urges the bio-signal sensor toward the extended position. In some embodiments, the user is able to manually adjust the extension of the bio-signal sensors. In some embodiments, the contact adjuster includes a plurality of extended positions and the user adjusts the bio-signal sensors into a desired extended position based on comfort and electrical contact between the bio-signal sensors and the skin.

In some embodiments, the wearable computing device includes a conduction medium applicator for providing a conduction medium to a skin-contacting surface of the bio-signal sensor. The conduction medium is electrically conductive and facilitates the electrical connection between the bio-signal sensor and the user's skin. In some embodiments, the conduction medium is a saline solution or a hydrogel. In some embodiments, the conduction medium has a viscosity of 1000-1300 cP. In some embodiments, the conduction medium has an impedance of less than 100 k$\Omega$.

In some embodiments, the mediated reality environment includes a virtual object interactable with the user via one or more stimulus modalities. For example, a virtual ball in a mediated reality environment may be associated with a visual stimulus such as color, patterns, size, and relative position of the ball; a pressure stimulus such as texture, compressibility or weight of the ball if a user "touches" or "lifts" the ball in the mediated reality; an auditory stimulus, such as the sound the ball makes as it "bounces" against ground. The one or more stimulus modality may simulate the properties of the object in the real world, or may be subject to properties as defined in the mediated reality.

In some embodiments, the wearable computing device includes at least one user input for the user to interact with the mediated reality environment. In some embodiments, the at least one user input includes a mouse, joystick, keyboard, controller, or any combination thereof. In some embodiments, the at least one user input includes tracking In some embodiments, the wearable computing device includes a tracker for measuring the position, orientation or location of the wearable device and the user's environment, such as 3-dimensional coordinates. In some embodiments, the tracker includes an inertial sensor for measuring movement of the wearable device, a gyroscope for measuring an orientation of the wearable device, an accelerometer for measuring movement of the wearable device, a GPS for measuring a user's location, light detection and ranging (LIDAR) systems, depth cameras, beam-forming microphone arrays and/or other environmental detection systems, or any combination thereof. In some embodiments, the tracker includes a gaze detector for detecting the user's gaze direction. In some embodiments, the gaze detector includes EOG sensors, an oculometer, or both.

In some embodiments, the wearable computing device includes a securement strap for securing the wearable computing device to a user. In some embodiments, the securement strap includes bio-signal sensors integrated therein. Securement straps are adjustable to accommodate different users. In some embodiments, the securement straps include elastic portions. In some embodiments, bio-signal sensors are integrated into the securement straps. Where the securement straps are disposed below a user's hairline, the integrated bio-signal sensors would not be required to penetrate the "mat" of a user's hair. Accordingly, in some embodiments, the integrated bio-signal sensors include a soft, deformable contact surface. In some embodiments, to increase comfort for the user, the soft, deformable contact surface is flush with the fixation strap.

Referring to FIG. 1 in accordance with an exemplary implementation of embodiments described herein, there is provided a perspective view of a wearable computing device 100. The wearable computing device includes a head mounted display 110 and a face pad 120.

Figure 2:
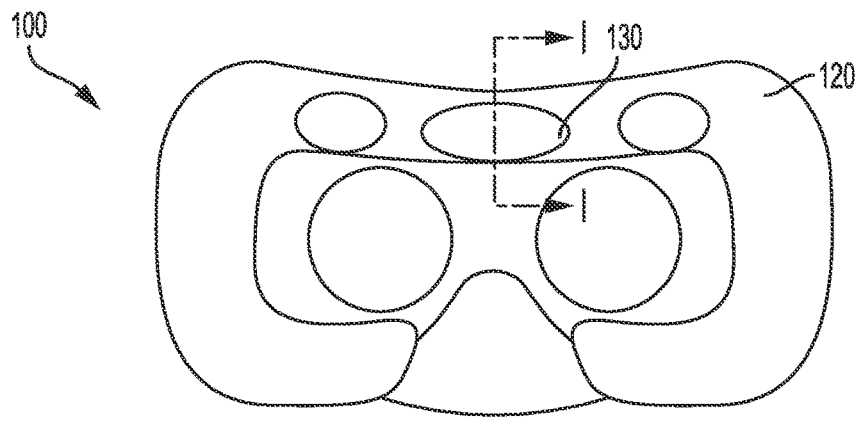
FIG. 2 illustrates a rear view of the wearable computing device of FIG. 1.

FIG. 2 illustrates a rear view of wearable computing device 100. The face pad 120 includes a foam pad 121 having an exterior surface 122 and an interior matrix 126. The exterior surface 122 may be formed as part of a foam molding process, or a surface applied thereafter. In some embodiments, the interior matrix 126 includes a soft foam. In some embodiments the interior matrix 126 includes an open cell foam. The open-cell foam is compressible such that when the wearable computing device 100 is affixed to a user's head, such that the foam pad 121 conforms to the user's face.

Face pad 120 may function as a display isolator for reducing or eliminating visual stimuli from sources other than head mounted display 110.

In some embodiments, face pad 120 is detachably attached to wearable computing device 100 (e.g. face pad 120 can be attached to and detached from the wearable computing device 100). In such embodiments, the face pad 120 may be a modular accessory configured to provide bio-signal sensor functionality to a VR headset.

As shown in FIG. 2, in some embodiments, face pad 120 includes bio-signal sensors disposed thereon. In some embodiments, the bio-signal sensors are electrodes 130. Electrodes 130 are distributed along the face pad 120 and may be spaced to minimize salt bridging effects. Salt bridging effects may arise, for example, due to a user's sweat or when electrodes are used with a conductive fluid, such as a saline solution or hydrogel. The salt bridge forms an electrical connection between electrodes and may lead to improper readings being obtained by the electrodes. In some embodiments, the distance between electrodes 130 is at least 3 cm, preferably at least 0.5 cm.

Figure 3:
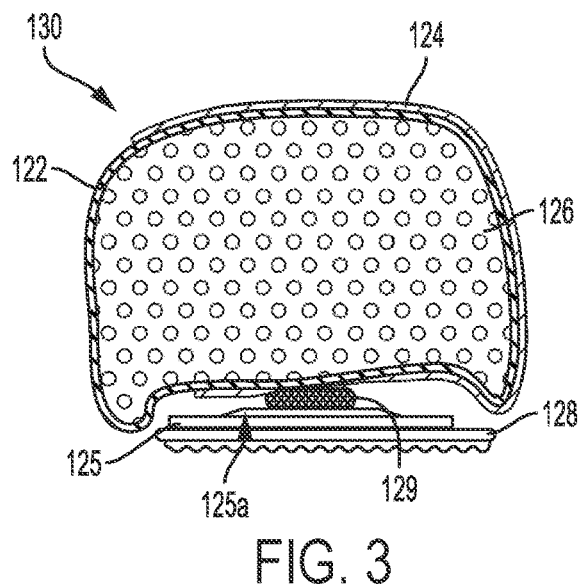
FIG. 3 illustrates a cross-sectional view taken along lines I-I of the wearable computing device of FIG. 2.

FIG. 3 is a cross-section taken along lines I-I of face pad 120 affixed to a backbone 128 and having electrodes 130. In some embodiments, the foam pad 121 is affixed to a backbone 128 with a conductive adhesive 129. In some embodiments, the conductive adhesive 129 connects the conductive coating 124 with an exposed conductive area 125a of a flexible printed circuit board (PCB) 125. The backbone 128 encloses the electronics, provides structure for the face pad 120, and attaches to the HMD, such as by velcro or other methods. In some embodiments, the backbone 128 is made from plastic, fabric, felt, metal, or combinations thereof, preferably plastic.

As shown in FIG. 3, in some embodiments, electrodes 130 includes a conductive coating 124. In some embodiments, a conductive coating 124 is applied to the exterior surface 122. The coating 124 extends to the rear of the foam pad 121 to connect to a sensor manifold (not shown). For example, the exterior surface 122 is masked and sprayed with the conductive coating 124. In some embodiments, the conductive coating 124 is PEDOT:PSS.

Figure 4:
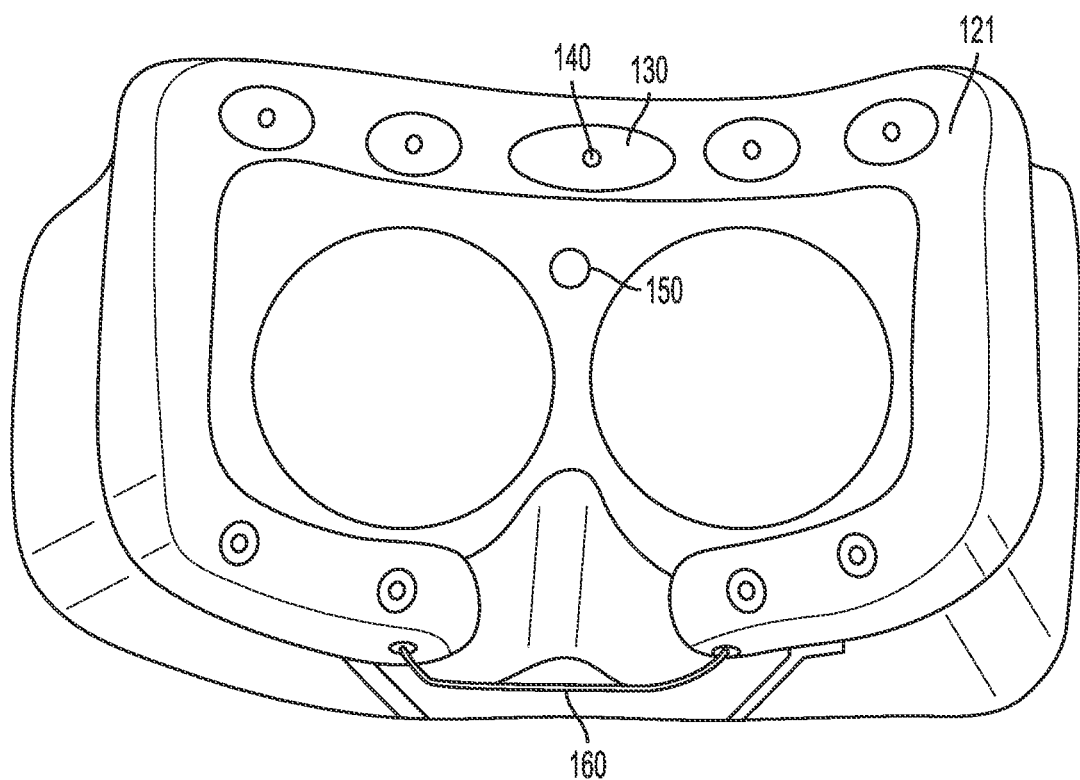
FIG. 4 illustrates a rear view of a wearable computing device, according to an embodiment.

As shown in FIG. 4, in some embodiments, the wearable computing device 100 includes an optical device 140 mounted on the foam pad 121 of face pad 120. In some embodiments, the optical device 140 is an optical receiver, transmitter, or optical receiver/transmitter pair. The optical device 140 may be used, for example, for fNIRS brain sensing, or visible light measurement of blood flow and oxygenation. In some embodiments, the optical device 140 is located proximate, surrounded by, or embedded in the electrode 130. The optical device 140 can capture additional bio-signals for processing in conjunction with brainwave signals. Times stamps and clock synchronization can be used, for example, the correlate multiple signal streams.

Figure 5:
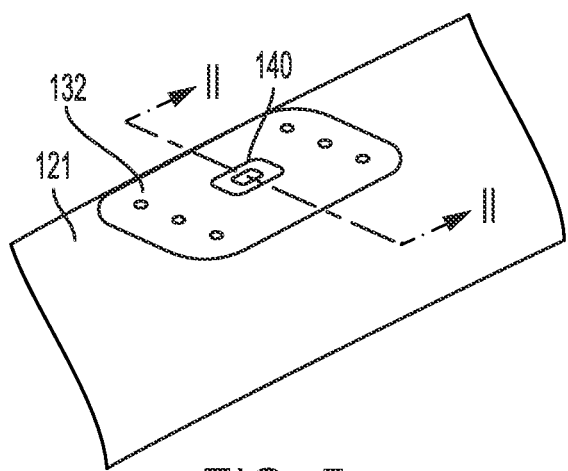
FIG. 5 illustrates a perspective view of a portion of a face pad of the wearable computing device of FIG. 4.
Figure 6:
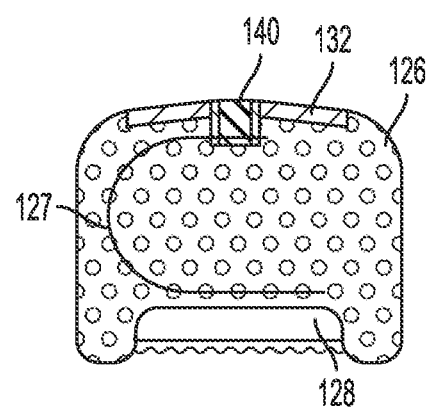
FIG. 6 illustrates a cross-sectional view taken along lines II-II of the portion of the face pad of the wearable computing device of FIG. 5.

FIG. 5 is a perspective view of a portion of foam pad 121 of wearable computing device 100 of FIG. 4. FIG. 6 illustrates a cross-sectional view taken along lines I-II of the portion of foam pad 121 of wearable computing device 100 of FIG. 5. The optical device 140 is connected to a flexible printed circuit board (PCB) 127 through the interior matrix 126. The accuracy of optical heart sensors might be improved depending on their proximity to arteries near the surface of the user's face, such as the facial artery and its various branches, including the lateral nasal artery and the angular artery. In some embodiments, the optical device 140 is an optical heart sensor located proximate a user's nose.

As shown in FIGS. 5 and 6, in some embodiments, the electrode 130 includes a soft portion 132. In some embodiments, the soft portion 132 includes a closed cell foam or an elastomer. In some embodiments, the closed cell foam is neoprene. In some embodiments, the elastomer is a soft, conductive elastomer. In some embodiments, the electrode 130 is a PEDOT:PSS coated neoprene. The PEDOT:PSS may be Clevious PH1000, dip coated or sprayed onto the soft portion 132.

Figure 7:
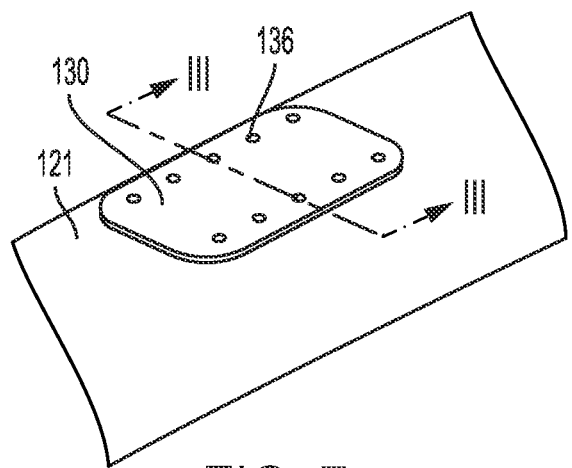
FIG. 7 illustrates a perspective view of a portion of a face pad of a wearable computing device, according to an embodiment.
Figure 9:
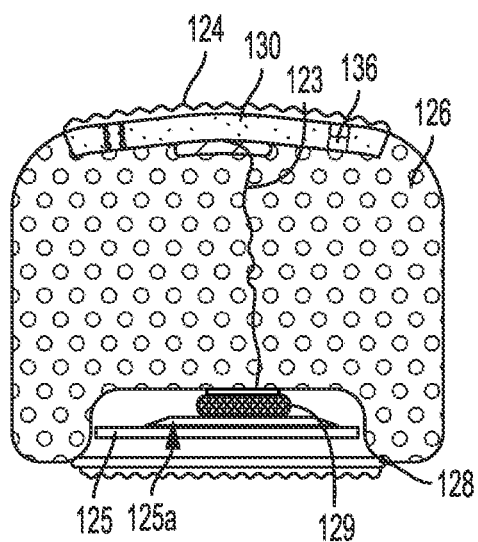
FIG. 9 illustrates a cross-sectional view taken along lines III-III of the portion of the face pad of the wearable computing device of FIG. 7.

In some embodiments, for example as shown in FIG. 7, electrode 130 includes detailing 136 to increase the conductivity between the front side and backside of the electrode 130 or the adhesion to foam pad 121. In some embodiments, detailing 136 includes a hole or channel disposed through or partially through the electrode 130, having conductive coating 124 disposed therethrough. FIG. 9 illustrates a cross-sectional view taken along lines Ill-Ill of the portion of foam pad 121 of wearable computing device 100 of FIG. 7. As shown, conductive adhesive 129 connects the conductive element 123 with an exposed conductive area 125a of a flexible printed circuit board (PCB) 125.

Figure 8:
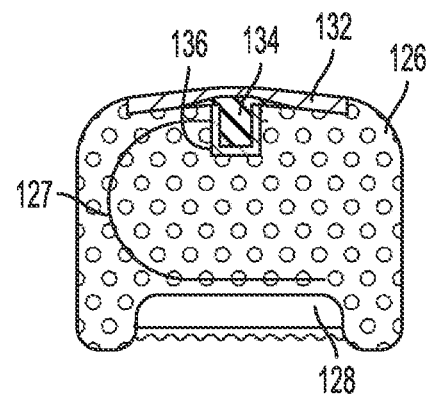
FIG. 8 illustrates a cross-sectional view of a face pad of a wearable computing device, according to an embodiment

FIG. 8 illustrates a cross-sectional view of a foam pad 121 of a face pad 120, according to an embodiment. In some embodiments, the electrode 130 includes a conductive base 134. The conductive base 134 may be made from plastic, metal, or combination thereof. In some embodiments, the base 134 is molded into soft portion 132 or attached with a conductive adhesive.

Figure 10:
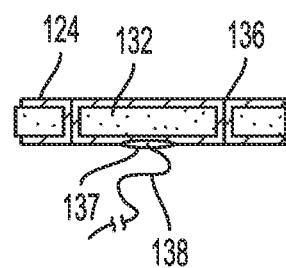
FIG. 10 illustrates a cross-sectional view of an electrode of a wearable computing device, according to an embodiment.

In some embodiments, for example, as shown in FIG. 10, a fixation member 137 connects electrode 130 with a flexible PCB 138, a conductive thread, or a wire. In some embodiments, the thread is a spun stainless steel thread.

Figure 28:
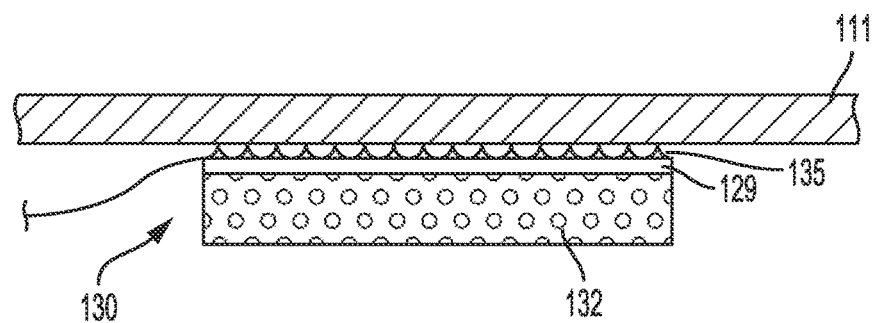
FIG. 28 illustrates a cross-sectional view of an electrode, according to an embodiment.

Having reference to FIG. 28, an alternative electrode 130 is shown. The electrode includes a soft portion 132. The soft portion 132 includes an open-cell foam that is optionally coated with a conductive layer, such as PEDOT:PSS. The foam is soaked with a conductive fluid prior to use. In some embodiments, the conductive fluid is saline, or an electrode gel/fluid. The electrode 130 has a conductive coating, such as conductive adhesive 129 as shown in FIG. 28, or flexible PCB for electrically connecting the soft portion with the HMD 110 or sensor electronics. In some embodiments, the electrode 130 is attached to the strap 111 by hook and loop connectors 135, such as Velcro.

Figure 29:
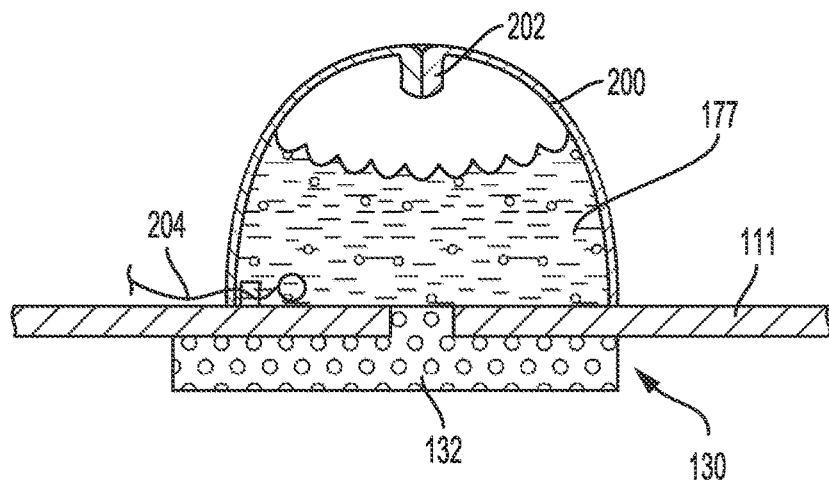
FIG. 29 illustrates a cross-sectional view of an electrode, according to an embodiment.

Having reference to FIG. 29, in some embodiments, a conductive fluid reservoir 200 may be fluidly connected to the soft portion for supplying conductive fluid 177 to the soft portion of the electrode 130. The reservoir 200 includes a refilling port 202 for supplying the reservoir 200 with conductive fluid 177. In some embodiments, an electrical connection 204 is provided. Use of conductive fluid 177 may reduce the impedance and may improve the connection over electrodes without conductive fluid.

Figure 23:
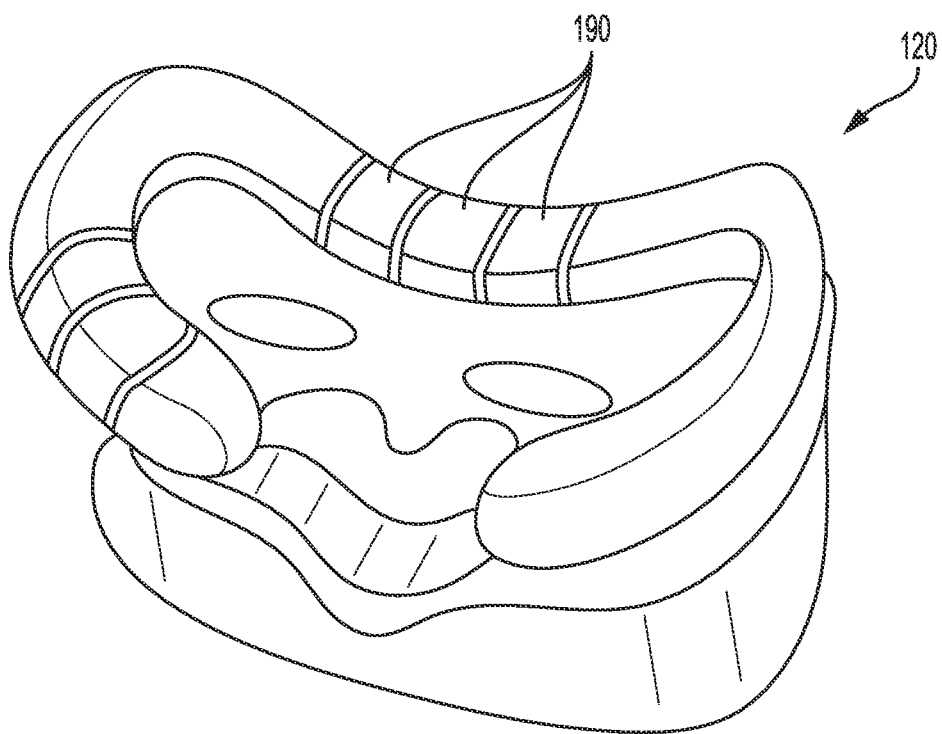
FIG. 23 illustrates a perspective view of a wearable computing device, according to an embodiment.
Figure 24:
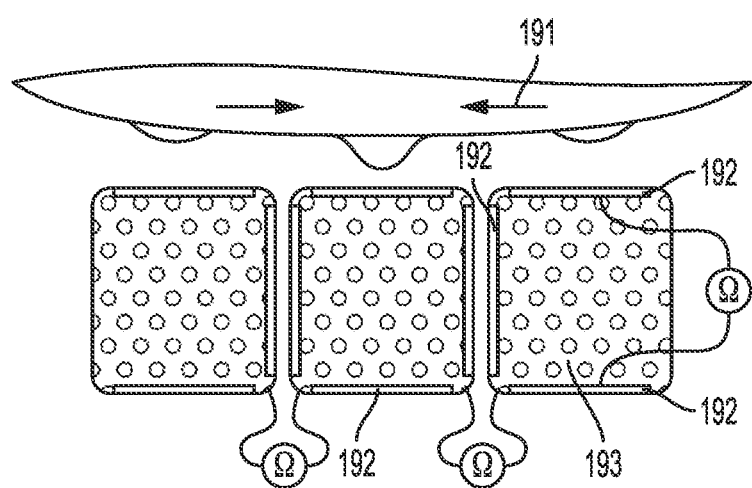
FIG. 24 illustrates a rear view of sensors of the wearable computing device of FIG. 23.

Having reference to FIGS. 23 and 24, in some embodiments, the face pad 120 includes pressure and/or strain sensors to measure face movement. The sensors augment other sensors, such as facial EMG, to determine the facial expression the user is exhibiting. In some embodiments, the pressure and/or strain sensors are in the form of segmented face cushions 190. Facial movement 191 causes differential pressure and compression of the segmented face cushions 190. Piezoelectric or printed strain sensors 192 on the surface of cushion 190 for measuring strain. The sensors 192 are aligned with the muscles of the face, such as the orbicularis oculi. The bulk impedance measurement through a conductive foam interior 193 of the cushion 190 can measure the compression of the cushion 190. In some embodiments, the surface of the cushion 190 includes conductive surfaces between adjacent segments to measure pressure changes between the segments caused by lateral movement of the skin. The movement causes the impedance between the segments to vary. In some embodiments, the cushion 190 includes a piezoelectric resistive or printed strain sensor 192 on a bottom surface of the cushion 190 to measure pressure.

Facial bio-signal sensors such as electrodes 130 or sensors 192 may further yield facial expression information (which may be difficult to obtain using cameras in a VR headset). Muscles specifically around the eyes play an important role in conveying emotional state. Smiles, for example, if accompanied by engagement of the muscles at the corners of the eyes are interpreted as true smiles, in contrast to those that are put on voluntarily. EOG signals provide information about eye movements. Basic gaze direction and dynamic movement can be estimated in real-time and can thus be used as a substitute for optical methods of eye tracking in many applications. In some embodiments, such information can be rendered on an object in a VR environment, for example, on the eye(s) of an avatar of the user in the VR environment. Measurement of the EOG signal is also important for noise free interpretation of the EEG signal. fNIRS sensors if used can provide supplemental information about activity in the frontal region of the brain with high spatial accuracy. Other sensors tracking other types of eye movement may also be employed.

In some embodiments, for example as shown in FIG. 4, the wearable computing device 100 includes an optical eye tracker 150 for user gaze tracking. In some embodiments, electrodes 130 are used to obtain EOG data for gaze tracking.

In some embodiments, for example as shown in FIG. 4, the wearable computing device 100 includes a breath sensor 160. When worn, the breath sensor 160 may be located proximate a user's nose. Having reference to FIG. 25a and 25b, breath sensor includes a turbulence inducer 162 and a pressure transducer 164 attached to a deformable armature 161. The deformable armature allows the user to adjust the breath sensor 160 to adjust it to an optimal position for their face. The pressure transducer 164 measures the pressure vibrations from the air flow due to a user's breathing. In some embodiments, the pressure transducer 164 includes an electret microphone, dynamic microphone, a piezo-electric device. The turbulence inducer 162 causes a user's breath flowing toward sensor 160 to increase in turbulence such that it can be detected by pressure transducer 164. The breath sensor 160 may be placed under the user's nose, or to the side. When placed under the user's nose, the pressure transducer better detects the lower frequency pressure modulations. Having reference to FIG. 26a, in some embodiments, the turbulence inducer 162 includes a grate. The turbulence inducer vibrates when a user's breath flows past. The vibration is detected by the pressure transducer 164. FIG. 26b illustrates a perspective view of the breath sensor 160 embodiment of FIG. 26a.

Having reference to FIG. 27, in some embodiments, the breath sensor 160 is integrated into a nose guard of a HMD and blocks stray light. In some embodiments, the turbulence inducer 162 is a series of ventilation holes.

Figure 11:
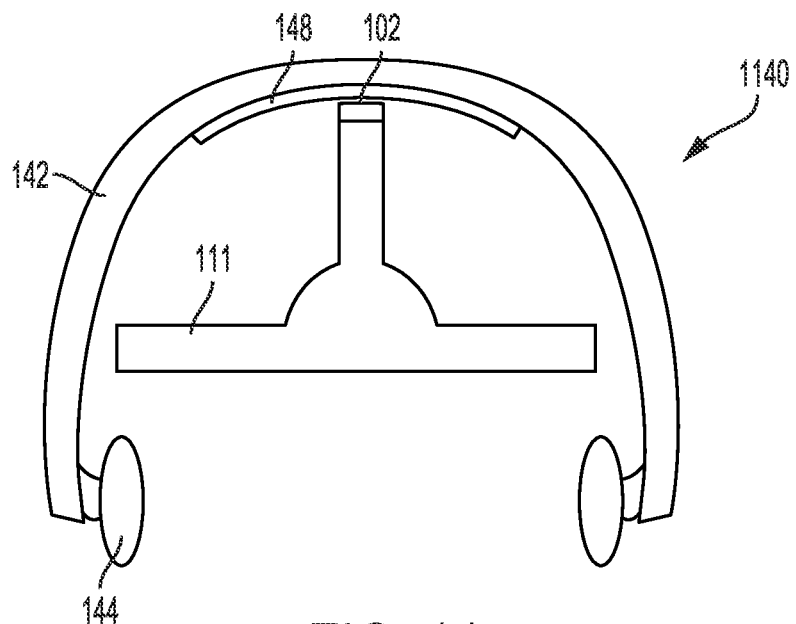
FIG. 11 illustrates a front view of a sound generator, according to an embodiment.
Figure 12:
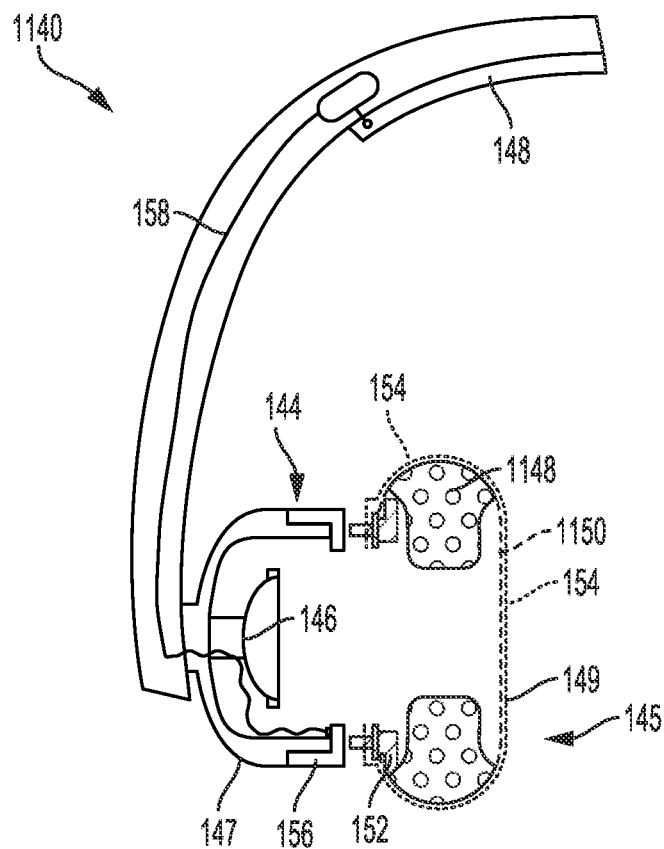
FIG. 12 illustrates a cross sectional area of the sound generator of FIG. 11.

Having reference to FIGS. 11 and 12, in some embodiments, the wearable computing device 100 includes a sound generator 1140. In some embodiments, the sound generator is a headphone including an armature 142 housing and headphone earpiece 144. In some embodiments, the breath sensor 160 is supported by the armature 142. The earpiece 144 includes a speaker 146 and electrodes 149. In some embodiments, the sound generator 1140 includes a conductive pad 148 electrically connecting to a conductive pad 102 of the wearable computing device 100. In some embodiments, the conductive pad 102 is disposed on a strap 111 of the HMD 110. The connection of the conductive pad 148 connects the electrodes 149 of the sound generator 1140 to the HMD 110. In some embodiments, the electrical connection is effected by the application of mechanical pressure. In some embodiments, the sound generator 1140 is used independently or without head mounted display 110. In some embodiments, the conductive pad 148 is used as an electrode to measure bio-signals if the headphones are used independently from the HMD 110.

In some embodiments, the earpiece 144 includes a pad 145 attached to an earpiece body 147. The pad 145 includes an interior 1148, an exterior surface 1150, and a coupler 152 for attaching the pad 145 to the earpiece body 147. In some embodiments, the interior 1148 is an open-cell foam. In some embodiments, the exterior surface 1150 is a thermoplastic urethane or a synthetic leather, or other suitable material for headphone earpads. The pad 145 includes a conductive coating 154 applied on the exterior surface 1150. The conductive coating 154 is electrically connected to a conductive flange 156 on the earpiece body. The conductive flange 156 connects to the conductive pad 148 via a wire 158. In some embodiments, additional electrical connection between the conductive flange 156, the conductive pad 148, and wire 158 is provided. The pad 145 includes electrodes 149 disposed thereon and are in electrical connection with the conductive coating 154. The electrodes 149 may be disposed on the pad 145 similar to how the electrodes 130 are disposed on the foam pad 121 of the HMD 110.

Figure 13:
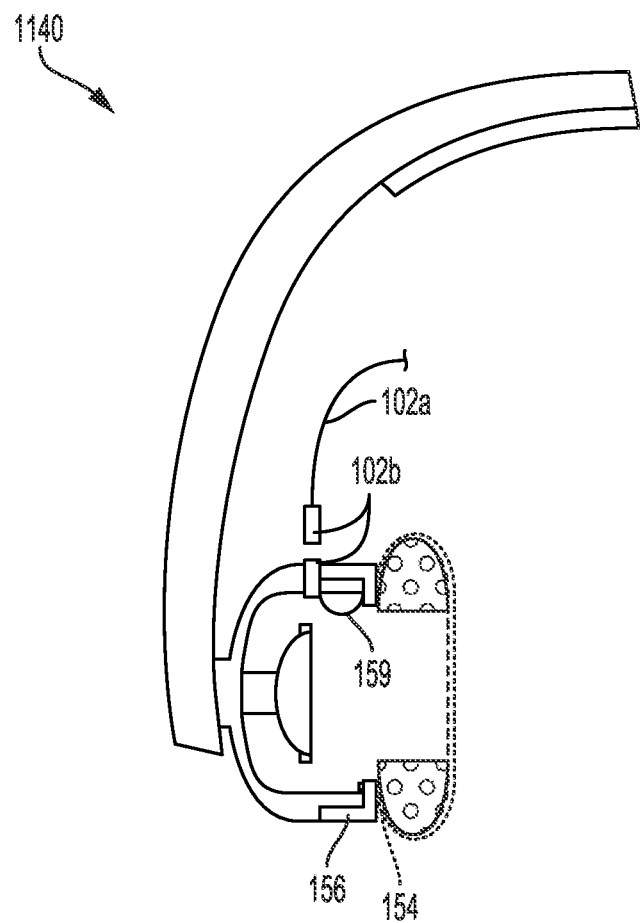
FIG. 13 illustrates a cross sectional area of a sound generator, according to an embodiment.

Having reference to FIG. 13, in some embodiments, the sound generator 1140 includes a connector 102b that provides electrical connection to a connector 102a of the HMD 110. In some embodiments, the connectors 102b and 102a include complementary 1.5 mm stereo audio connectors or magnetic connectors. In some embodiments, a wire 159 electrically connects the connector 102b and the conductive coating 154.

Figure 14:
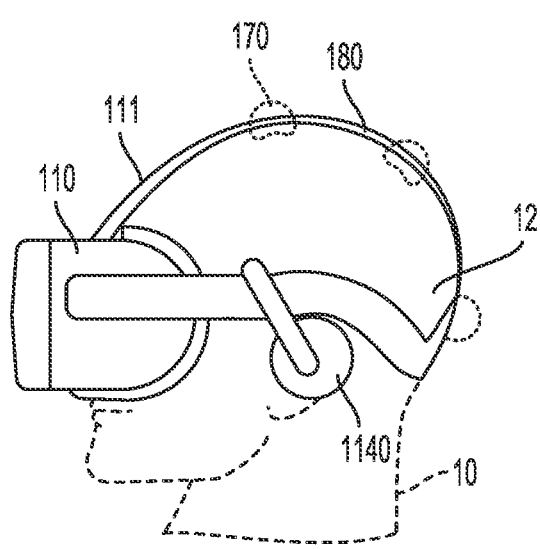
FIG. 14 illustrates a side view of a user wearing a wearable computing device according to an embodiment.
Figure 15:
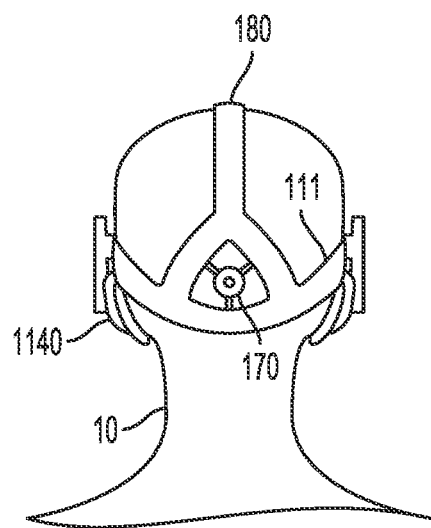
FIG. 15 illustrates a rear view of the user wearing the wearable computing device of FIG. 14.

FIG. 14 illustrates a side view of a user 10 wearing a wearable computing device 100, according to an embodiment. As shown in FIG. 14, when worn, strap 111 of wearable computing device 100 fixes the HMD 110 on user 10. The strap 111 includes bio-signal sensors such as electrodes 170 for obtaining bio-signals from the scalp or skin 12 of user 10. The strap 111 optionally includes other bio-signal sensors such as non-contact electrodes 180. FIG. 15 illustrates a rear view of user 10 wearing wearable computing device 100 according to the embodiment shown in FIG. 14.

Figure 16:
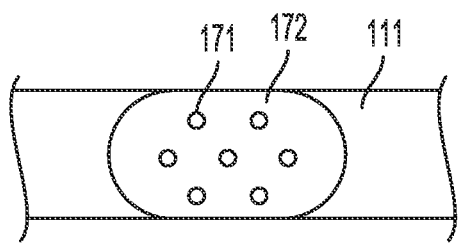
FIG. 16 illustrates a bottom view of a scalp-contacting electrode, according to an embodiment.
Figure 17:
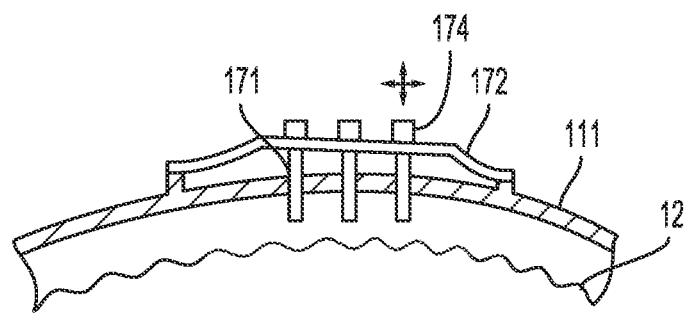
FIG. 17 illustrates a side view of the electrode of FIG. 16.

Having reference to FIGS. 16 and 17, in some embodiments, electrode 170 includes electrode pins 174 attached to the strap 111 by biaser 172. The strap 111 defines apertures 171 sized to receive the electrode pins 174. The electrode pins 174 may be made of conductive or nonconductive plastic with a conductive coating applied thereon. Alternatively, the pins 174 may include a replaceable hydrogel tip. The electrode pins 174 are perpendicularly displaceable with respect to the strap 111. When the HMD 110 is worn, the electrode pins 174 first make contact against the user's scalp. As the strap 111 is tightened, the electrode pins 174 move relative to the strap 111 through the apertures 171. The biaser 172 resists this movement and applies pressure keeping the electrode pins 174 against the scalp. This allows the pressure to be distributed on the user's scalp between the strap 111 and the electrode pins, as compared to a fixed electrode pin where all pressure is applied at the electrode pin, thereby reducing the amount pressure acting on the scalp at the electrode pins 174. In some embodiments, the biaser 172 is a deformable base. In some embodiments, the deformable base includes an elastomer retaining the base. In some embodiments, the elastomer is a soft elastomer, such as 40A durometer silicone rubber.

Figure 18:
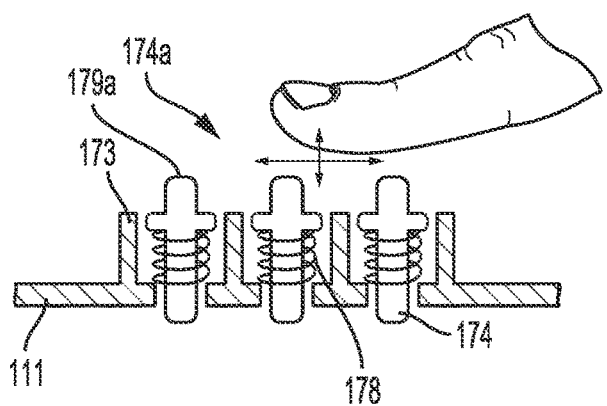
FIG. 18 illustrates a side view of a scalp-contacting electrode, according to an embodiment.

Having reference to FIG. 18, in some embodiments, the biaser 172 includes pin guides 173, each pair of pin guides 173 attached to a spring 178. In some embodiments, the electrode pin 174 includes an adjustment portion 179a allowing a user to manually adjust the electrode pin 174 to move it through the user's hair to make contact with the user's scalp, for example, by wiggling the pin 174.

Figure 19:
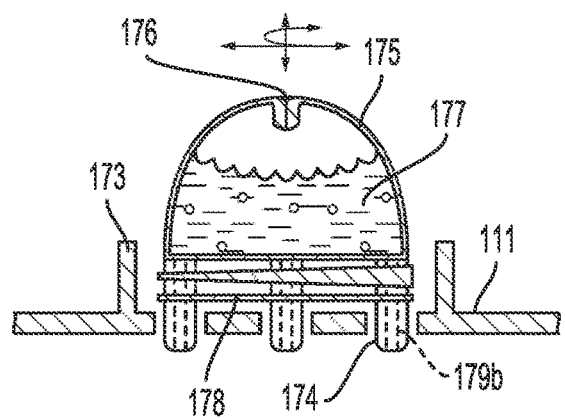
FIG. 19 illustrates a side view of a scalp-contacting electrode having a conductive fluid reservoir, according to an embodiment.
Figure 20:
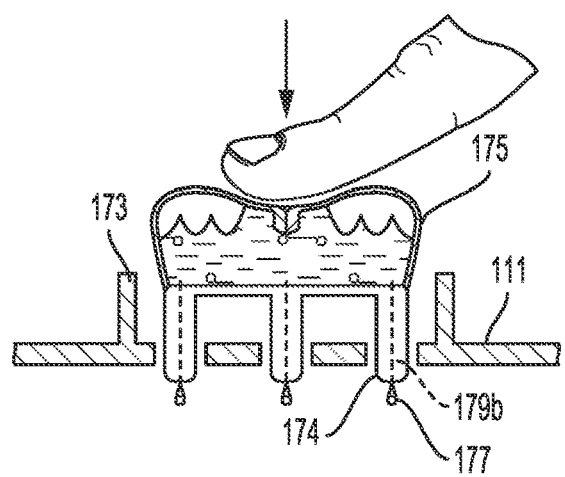
FIG. 20 illustrates a side view of the scalp-contacting electrode of FIG. 19 dispensing conductive fluid.

FIG. 19 illustrates a side view of a scalp-contacting electrode 170 having a conductive fluid reservoir 175, according to an embodiment. FIG. 20 illustrates a side view of the scalp-contacting electrode of FIG. 19 dispensing conductive fluid 177.

As shown in FIGS. 19 and 20, in some embodiments, electrode 170 may include a conductive fluid reservoir 175 containing a conductive fluid 177 therein. Electrode pins 174 may be biased against skin 12 of user 10 by spring 178 attached to pin guides 173. The electrode pin 174 includes a conduit 179b for receiving conductive fluid from the reservoir 175 to distribute the conductive fluid to the tip of the of electrode pin 174. The conduit 179b is sized depending on the viscosity of the conductive fluid. In some embodiments, the reservoir 175 includes a loading port 176 for refilling the reservoir 175 with conductive fluid 177. In some embodiments, the reservoir 175 is deformable, thereby pressurizing the conductive fluid in the reservoir 175 and urges the conductive fluid 177 through the conduit 179b. In some embodiments, the reservoir 175 is filled with a syringe or suctions conductive fluid from a conductive fluid source by first depressing the reservoir 175.

Figure 21:
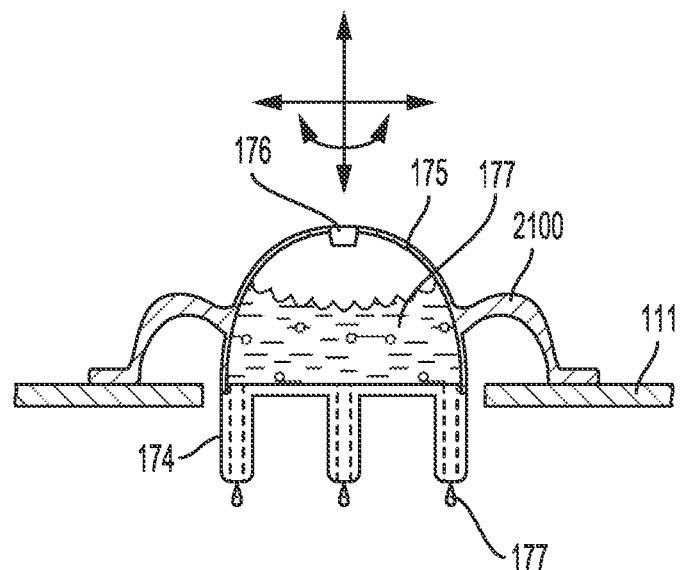
FIG. 21 illustrates a side view of a scalp-contacting electrode having a conductive fluid reservoir, according to an embodiment.
Figure 22:
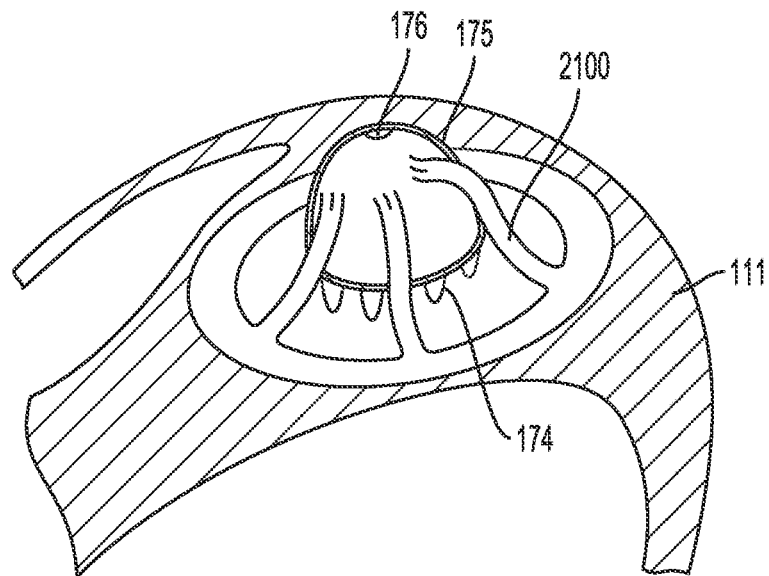
FIG. 22 illustrates a perspective view of the scalp-contacting electrode of FIG. 21.

FIG. 21 illustrates a side view of a scalp-contacting electrode having a conductive fluid reservoir 175, in an embodiment. FIG. 22 illustrates a perspective view of the scalp-contacting electrode of FIG. 21. As shown in FIGS. 21 and 22, conductive fluid reservoir 175 may be attach to strap 111 by one or more supports 2100. In some embodiments, support 2100 may be deformable, and may include an elastomer. In some embodiments, the elastomer is a soft elastomer, such as 40A durometer silicone rubber.

Figure 39:
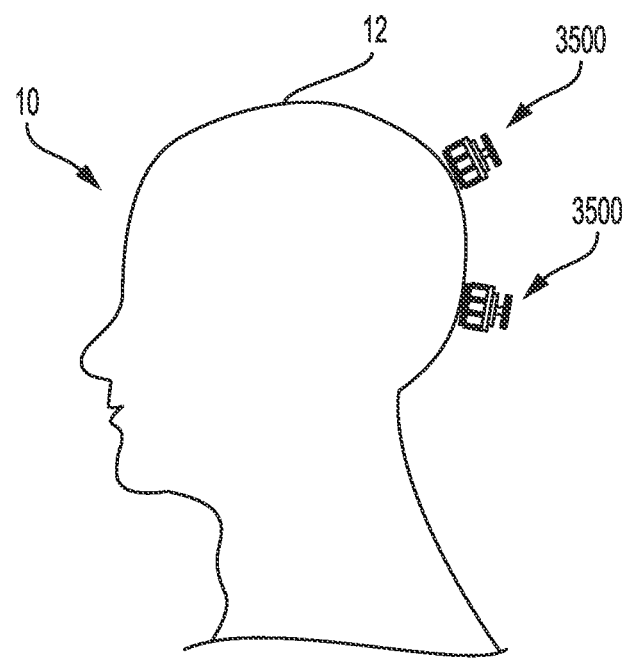
FIG. 39 illustrates a schematic view of placement of bio-signal sensors on a user, according to an embodiment.
Figure 40:
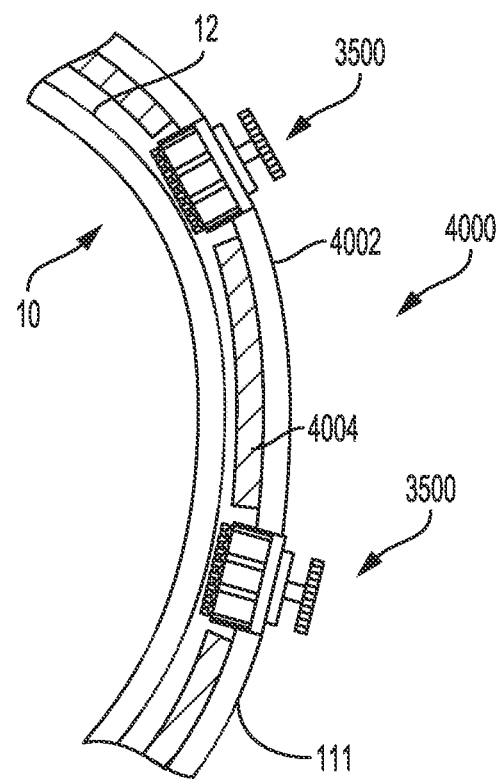
FIG. 40 illustrates a schematic view of placement of bio-signal sensors on a user, according to an embodiment.

In accordance with an aspect of the embodiments described herein, strap 111 may include sensors such as bio-signal sensors 3500 for obtaining bio-signals from the scalp or skin 12 of user 10. With reference to FIG. 39, there is provided a bio-signal sensor 3500. The sensor 3500 is configured to receive a bio-signal from a user 10, preferably, from the user's head or through the skin 12 of user 10. With reference to FIG. 40, the bio-signal sensor 3500 can be included on an apparatus 4000, for example on a support portion 4002 such as strap 111 of wearable computing device 100. The apparatus 4000 optionally includes at least one deformable portion 4004, for example, made from foam, connected to the support portion 4002 to provide comfort and/or support when the apparatus 4000 is worn by the user 10.

Figure 36:
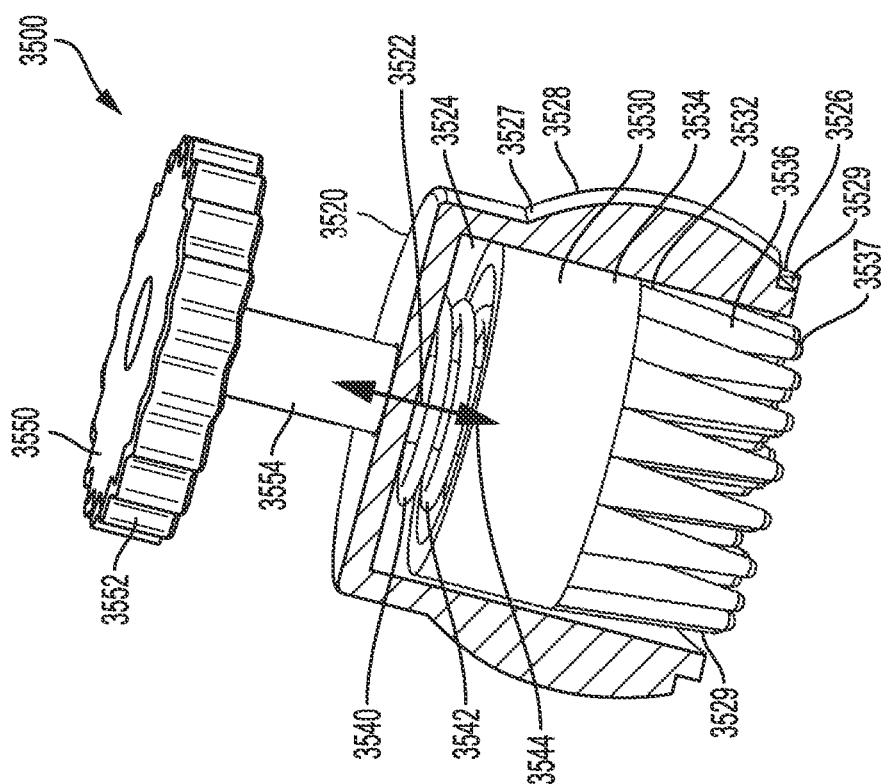
FIG. 36 illustrates a partial cross-sectional view of the bio-signal sensor of FIG. 35 in a compressed state.
Figure 35:
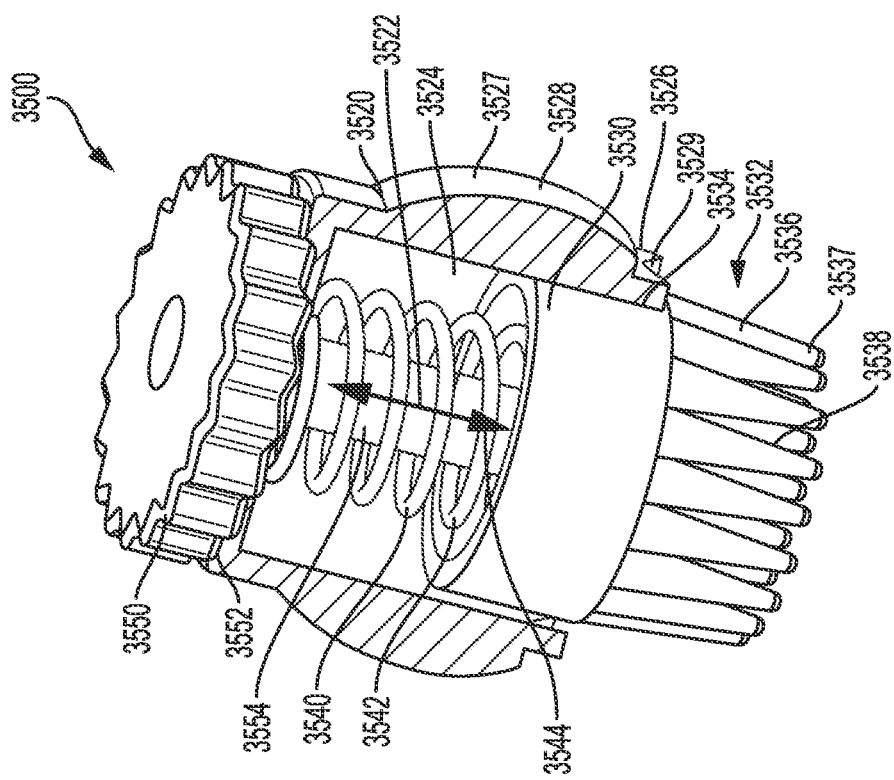
FIG. 35 illustrates a partial cross-sectional view of a bio-signal sensor in an uncompressed state, according to an embodiment.

With reference to FIGS. 35 and 36, the bio-signal sensor 3500 includes a body 3520, having a spherical portion 3528; an electrode 3530 extendable into the body 3520, the electrode 3530 having a contact end 3532 configured to receive an electrical bio-signal from a user's 10 skin 12, wherein in response to a downward force acting on the bio-signal sensor 3500 to urge the bio-signal sensor 3500 against the user's skin 12 and upon contact with the skin 12 of user 10, the electrode 3530 is configured for movement into the body 3520 along a movement axis 3522; an actuator 3540 operatively connected to the electrode 3530 for urging the electrode 3530 out of the body 3520 along the movement axis 3522 toward an extended position, wherein in the absence of the downward force, the electrode 3530 is disposed in the extended position; and a contact adjuster 3550 connected to the electrode 3530, the contact adjuster 3550 includes a handle 3552 manipulatable by the user to reduce noise the electrical bio-signal caused by impedance of the user's hair.

In use, a force having a downward component is applied to urge the bio-signal sensor 3500 against the skin 12 of user 10 to receive an electrical signal from the user 10. The electrode 3530 moves along the movement axis 3522 into an electrode receiving space 3524 of body 3520 from an extended position toward a retracted position (see, for example, FIG. 36). However, the user's hair may impede the ability of the bio-signal sensor 3500 to receive an electrical signal from the skin 12 of user 10. For example, the user's hair may form a barrier (or "mat") that acts as an insulation layer between the contact end and the user's skin. The insulation layer impedes or prevents the receiving of the electrical signal. As such, in some embodiments, the bio-signal sensor 3500 is configured to reduce the impedance effects of the user's hair.

In some embodiments, the contact end 3532 of the electrode 3530 includes a collection plate 3534 and a plurality of prongs 3536 extending from the collection plate 3534. Each prong includes a distal tip 3537 for contacting the skin 12 of user 10. Whereas with an electrode having a single contact surface, the user's hair may form a mat under the single contact surface, an interstitial volume 3538 defined by the prongs 3536, the collection plate 3534, and the skin 12 of user 10 may receive the user's hair and reduce or prevent the formation of a mat under the distal tips 3537 of the prongs. In some embodiments, the extension of the electrode 3530 from the body 3520 in the extended position is adjustable using the contact adjuster 3550. In some embodiments, contact adjuster 3550 includes a compression fitting, or threading that mates with the electrode or the body for adjusting the extension of the electrode 3530 in the extended position. The extension of the electrode 3530 from the body 3520 accommodates users with different volumes of hair. For example, a user with thick, long hair, may have a relatively greater volume of hair, which may create an electrical barrier if a mat is formed. For such users, the extended position may be adjusted such that the electrode 3530 extends further from the body 3520 than for users with shorter or no hair.

In some embodiments, the contact adjuster 3550 is configured to move the electrode along the movement axis 3522. In some embodiments, the handle is configured for lifting the electrode 3530 when urged against the skin 12 of user 10 and repositioning the electrode for placement against the skin 12 of user 10. In some embodiments, the movement of the contact adjuster 3550 moves the plurality of the prongs 3536 collectively. For example, in some embodiments, the contact adjuster 3550 is connected to the collection plate 3534 and is configured to move the collection plate. The movement of the collection plate 3534 causes the plurality of prongs 3536, which extend from the collection plate 3534, to move.

On the application of a downward force, the electrode 3530 moves along the movement axis 3522 into the body 3520 (see FIG. 36). Where there is significant retraction of the electrode 3530 into the body 3520, the body 3520 may become proximal to the skin 12 of user 10. This may cause, for instance, the user's hair disposed under the body 3520 of the sensor 3500 may form a barrier layer preventing good contact between the electrode 3530 and the skin 12 of user 10. Thus, in some embodiments, the body 3520 includes a contact end 3526 including at least one groove 3529 for receiving at least a portion of the user's hair therein.

In order to provide better comfort for a user, the pressure of the electrode 3530 against the skin 12 of user 10 may not be excessive. In some embodiments, the distal tips 3537 of the plurality of prongs 3536 are rounded. In contrast to a pointed tip, a rounded tip distributes the force applied to the skin over a greater area. In some embodiments, the radius of the distal tip is between about 0.25 mm and about 1 mm. In some embodiments, the radius of the distal tip is about 0.5 mm. The number and spacing of the prongs 3536 are selected such that the pressure applied to the skin 12 of user 10 is not excessive and has sufficient contact area to receive good adequate signal from the user's skin while maintaining sufficient void volume between prongs 3536 to receive the user's hair. In some embodiments, the electrode 3530 has a prong density of about 15 to 40 prongs per square centimeter. In some embodiments, the electrode 3530 has a prong density of about 25 pins per square centimeter.

A greater area of the contact end of the electrode 3530 may provide better electrical readings. However, when the area is too large, it may not conform well to the skin. One reason for this is that the skin is, typically, not perfectly flat. Increased area of the contact end of the electrode also increases the likelihood that the skin's curvature bends away, resulting in a loss of contact for the electrode. Thus, in some embodiments, the area of the contact end of the electrode 3530 comprising the prongs 3536, including the interstitial area between prongs, is between about 1 cm$^2$ and about 3 cm$^2$. In some embodiments, the area of the contact end of the electrode 3530 comprising the prongs, including the interstitial space between prongs, is about 1.5 cm$^2$. In some embodiments, the shape of the contact end 3532 of the electrode is round or polyhedral. The shape of the contact end 3532 may help move the user's hair to reduce or prevent the impedance effects of the user's hair.

In some embodiments, the contact adjuster 3550 is configured to rotate the electrode along a plane that is substantially perpendicular to the movement axis. The rotational movement may move the hair disposed under the sensor 3500. In some embodiments where the sensor includes a plurality of prongs 3536, the rotational movement may move the hair into the interstitial volume 3538. In some embodiments, the rotational movement of the contact adjuster 3550 is unrestricted. In some embodiments, the rotational movement of the contact adjuster 3550 is limited.

In some embodiments, the actuator 3540 includes a spring, a piston, a compressible material, or combination thereof. In some embodiments, the actuator 3540 includes a spring 3542. In some embodiments, the spring 3542 is a coil spring. The spring 3542 is disposed within the electrode receiving space 3524 such that one end is biased against an upper end 3526 of the body against the electrode 3530 such that the electrode 3530 is urged away from the electrode receiving space 3524 toward the extended position. In some embodiments, the spring 3542 biases against an upper end of the collection plate 3532 of the electrode 3530. When a downward force is applied to the sensor 3500 and when the electrode 3530 is against the skin 12 of user 10, the spring 3542 resists the movement of the electrode 3530 into the body 3520 such that a force is translated to the electrode 3530 urging it against the skin 12 of user 10.

In some embodiments, the spring 3542 is fixed on one end to the body 3520 and biased against the electrode 3530 on the other end, and wherein the contact adjuster 3550 includes a shaft 3554 extending through a compressive axis 3544 of the spring 3542 for translating rotational forces perpendicular to the movement direction from the handle 3552 to the electrode 3530, translational forces along the movement direction from the handle to the electrode, for both. In some embodiments, the compressive axis is co-axial or substantially co-axial with the movement axis 3522. In some embodiments where the spring 3542 is a coil spring, the coils of the coil spring are coiled around the shaft 3554 of the contact adjuster 3550.

In some embodiments, the actuator 3540 includes a plurality of actuators (not shown) corresponding to the plurality of prongs 3536. In some embodiments, the plurality of actuators individually bias the prongs against the skin 12 of user 10. This may allow, for instance, better conformity of the sensor against the skin 12 of user 10 as the skin may not be perfectly flat.

Figure 37:
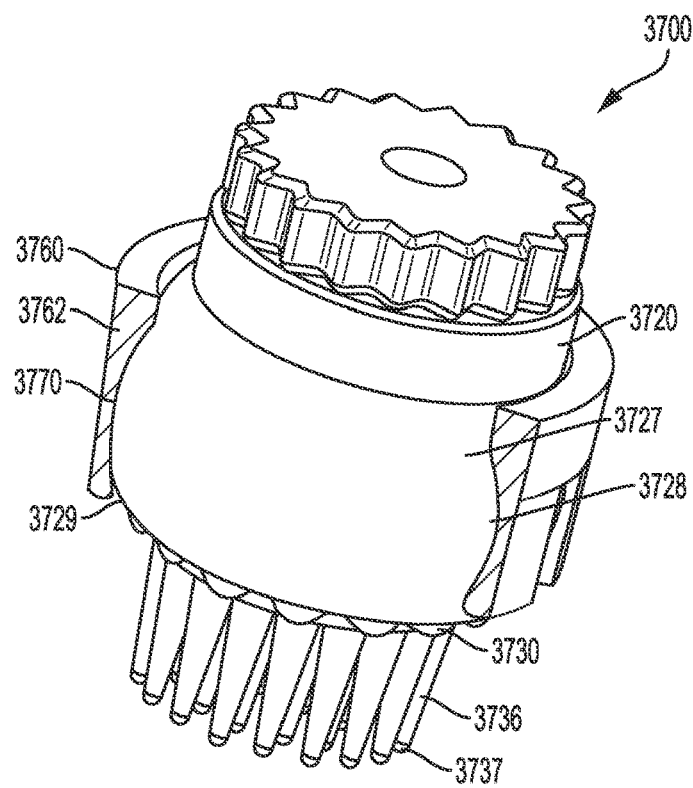
FIG. 37 illustrates a partial cross-sectional view of a bio-signal sensor, according to an embodiment.

The electrical bio-signal received by the electrode 3530 may be transmitted to a signal receiver, such as a processor or other computing device (not shown). In some embodiments, the signal receiver receives the electrical bio-signal from the body 3520 of the sensor. In some embodiments, the body includes a conductive portion 3527 for receiving the electrical bio-signal from the electrode. The conductive portion 3527 may be a conductive coating, a conductive material integrated into the body, or both. In some embodiments, the conductive coating is a conductive paint, such as a metallic paint, or a carbon paint. In some embodiments, the metallic paint includes silver, gold, silver-silver chloride, or a combination thereof. In some embodiments, the conductive material is a carbon-loaded plastic, or a conductive metal. In some embodiments, the body is 3D printed with a conductive material incorporated therein. In some embodiments, impedance between the electrode and a connection on the sensor for a wire from the signal receiver is less than about 1 kΩ. In some embodiments, the impedance between the electrode and the connection on the sensor is from about 1Ω to about 500Ω. In some embodiments, the connection is on the body 3520 or on a housing 3760 of a sensor 3700 shown in FIG. 37.

In some embodiments, the actuator 3540 electrically connects the electrode 3530 to the body 3520. For example, an electrical bio-signal may be transmitted from the electrode 3530 to the body 3520 via the actuator 3540. In some embodiments where the actuator 3540 includes a spring 3542, the spring 3542 is conductive. For example, a spring 3542 biased on one end against a collection plate 3534 and on the other end against the body 3520, the spring may act as a conductor.

Figure 38:
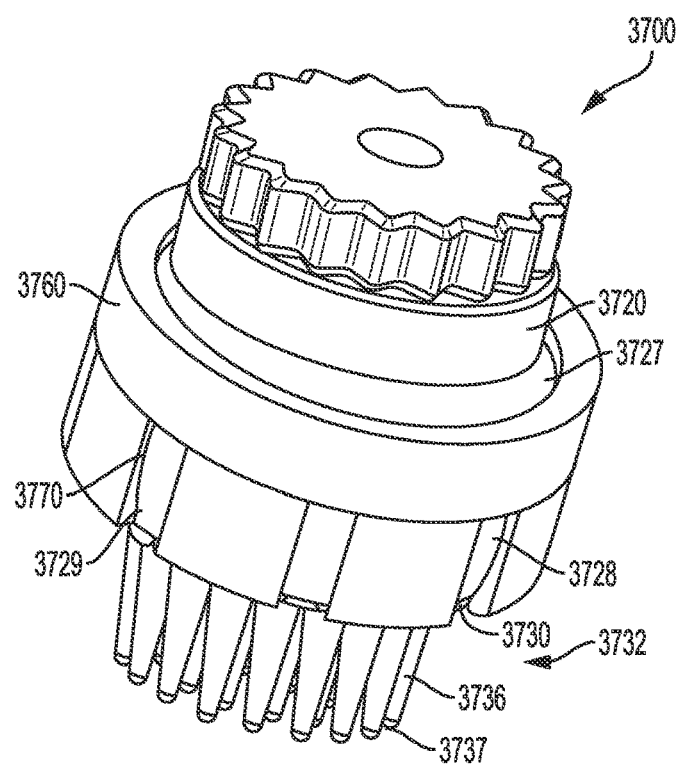
FIG. 38 illustrates a perspective view of the bio-signal sensor of FIG. 37.

In accordance with an aspect of the embodiments described herein, strap 111 may include sensors such as bio-signal sensors 3700 for obtaining bio-signals from the scalp or skin 12 of user 10. Having reference to FIGS. 37 and 38, in some embodiments, a sensor 3700 includes a gimbal 3770 configured to orient the electrode 3730 normal or substantially normal to the skin 12 of user 10. A normally oriented electrode 3730 may have better contact with the user's skin. For example, where prongs 3736 are the same length, a normal orientation prevents the angular contact with the user's skin where certain prongs are not lifted off from the user's skin. Further, where the electrode 3730 contacts the skin at an angle, one or more of the prongs 3736 may be pushed up by the hair. In some embodiments, body 3720 includes a spherical portion 3728, wherein the sensor further includes a housing 3760 defining a joint portion 3762 configured to receive the spherical portion 3728 of the body 3720 such that the gimbal 3770 includes the spherical portion 3728 and the joint portion 3762. In some embodiments, the spherical portion 3728 is removably receivable by the joint portion 3762. In some embodiments, the interface between the joint portion 3762 and the spherical portion 3728 includes a friction reducing agent. In some embodiments, the friction reducing agent is a carbonaceous material. In some embodiments, the carbonaceous material is integral to at least a portion the body 3720, the housing 3760, or both. In some embodiments, the housing 3760 includes an electrical connection portion for establishing an electrical connection between the sensor 3700 and a signal receiver.

In some embodiments, body 3720 includes at least one groove 3729 for receiving at least a portion of the user's hair therein.

In some embodiments, at least a portion of the conductive portion 3727 is disposed in or on the spherical portion 3728. In some embodiments, the electrical bio-signal received from the electrode 3720 is transmitted to the housing 3760 from the body 3720. In these embodiments, the signal received may connect to the housing 3760. In some embodiments where a friction reducing agent is included, the friction reducing agent includes or is a conductivity modifier to improve impedance. In some embodiments, the conductivity modifier is a metal powder, graphite, carbon nanotubes, metal-coated glass or plastic beads. For example, where the friction reducing agent is a carbonaceous material integral to the body 3720, the carbonaceous material may provide both friction reduction and conductivity. In some embodiments, a wire on a support portion 4002 of a head-mounted apparatus 4000 is connected at one end to the sensor 3700.

Figure 41:
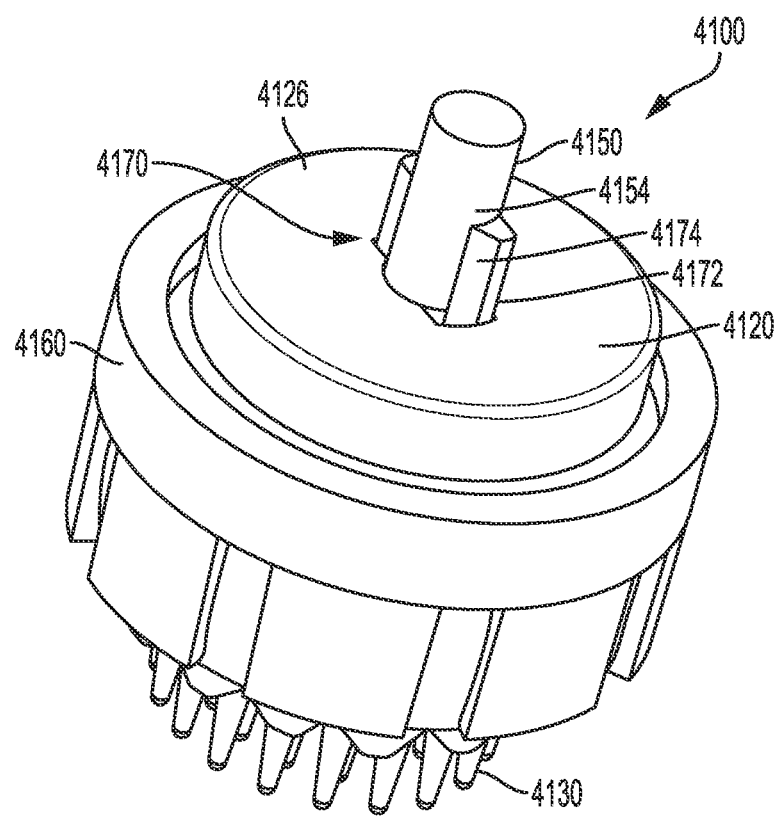
FIG. 41 illustrates a perspective view of a bio-signal sensor, according to an embodiment.
Figure 42:
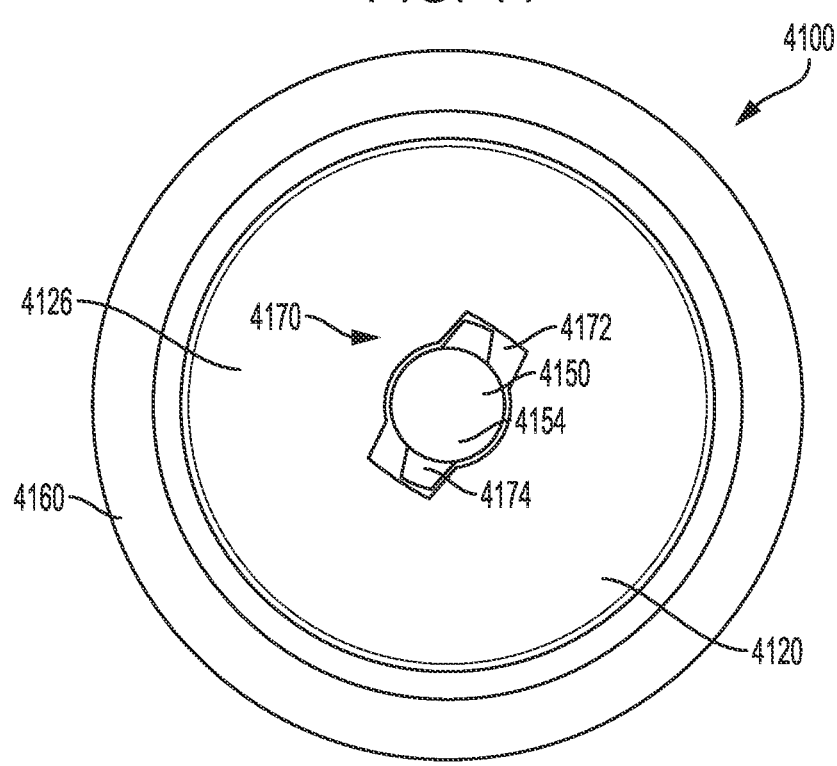
FIG. 42 illustrates a top view of the bio-signal sensor of FIG. 41.

Having reference now, to FIGS. 41 and 42, in some of the embodiments where the rotational movement is limited, the sensor 4100 includes a rotational limiter 4170 for limiting the rotational movement of the electrode 4130. If the hair is rotated excessively in a single direction, the hair may become wrapped or tangled. In some embodiments, the rotational limiter allows an oscillatory movement along a rotational axis for the electrode to get between the user's hairs. In some embodiments, the rotational limiter limits the rotational movement to at least about 0.25 radians. In some embodiments, the rotational limiter 4170 includes a slot 4172 and a key 4174 configured to rotate restrictively within the slot 4172. The movement of the electrode 4130 with respect to the body 4120 are limited by the slot 4172 and the key 4174. In some embodiments, the upper end 4126 of the body 4120 defines the slot 4172 and the shaft 4154 of the contact adjuster 4150 includes the key 4174. In some embodiments, the rotational limiter includes a stop disposed in the body, the electrode, the shaft, or any combination thereof. In some embodiments, a housing 4160 is configured to receive body 4120.

In some embodiments, a light connected to the processor indicates a brain state at the sensor 3500 or sensor 3700. In some embodiments, the brightness or color of the light is modified according to an event in the brain, such as an event related potential, a continuous EEG, a cognitive potential, a steady state evoked potential, or combination thereof. In some embodiments, the light is integral with the sensor or mounted proximate the sensor on a support portion of a head-mounted apparatus.

Figure 30:
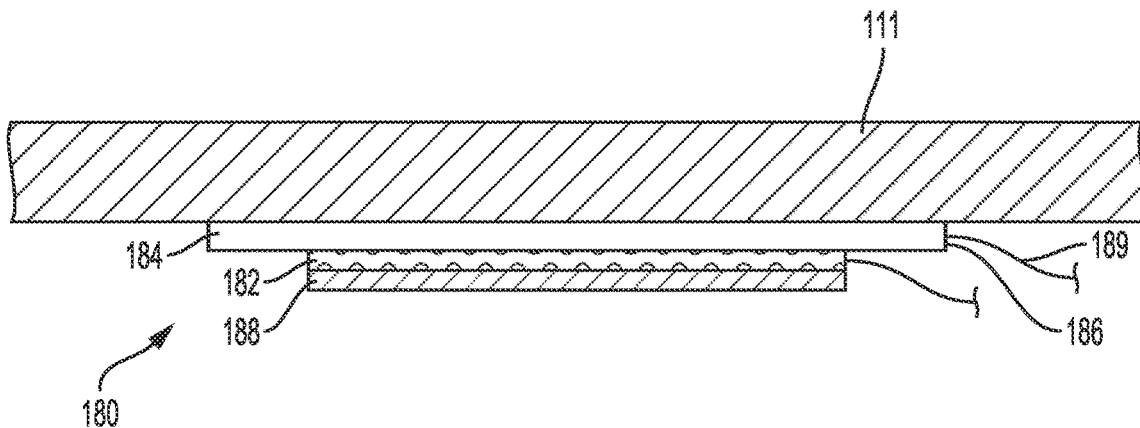
FIG. 30 illustrates a non-contact electrode, according to an embodiment.

Having reference to FIG. 30, in some embodiments, non-contact electrodes 180 include a conductive layer 182 and a conductive noise layer 184 with a dielectric layer 186 disposed therebetween. The conductive noise layer 184 reduces the noise in the signal obtained by the electrode 180. The conductive noise layer 184 may be an active guard or a ground plane. In some embodiments, a dielectric layer 188 is applied to a user facing side of the conductive layer 182. The conductive layer 182 connects to the HMD 110 or sensor electronics via a wire 189.

Figure 43:
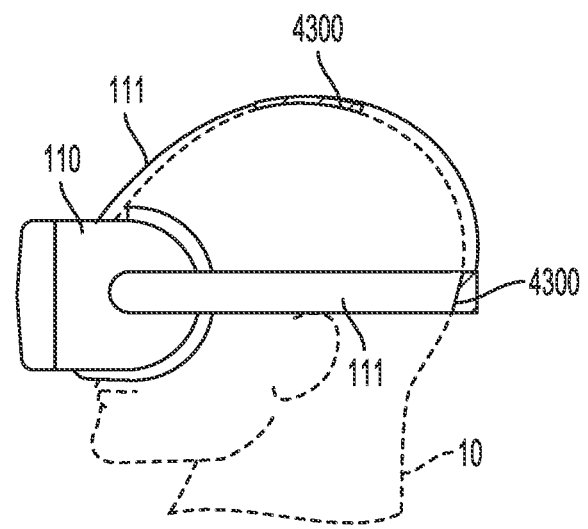
FIG. 43 illustrates a side view of a user wearing a wearable computing device having a capacitive electrode, according to an embodiment.
Figure 44:
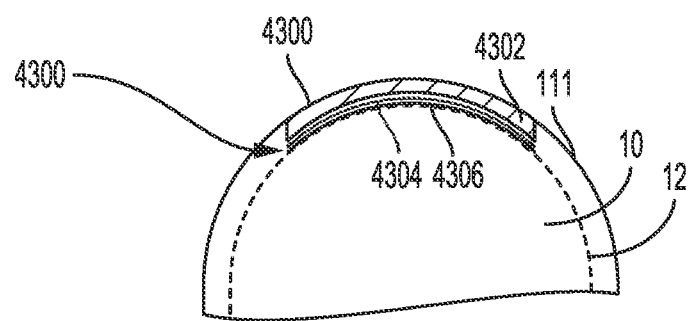
FIG. 44 illustrates a partial top view of the wearable computing device of FIG. 43.

In some embodiments, a non-contact electrode may take the form of capacitive electrode 4300, as shown in FIG. 43. FIG. 43 illustrates a side view of user 10 wearing a wearable computing device 100 having a bio-signal sensor in the form of a capacitive electrode 4300, according to an embodiment. FIG. 44 illustrates a partial top view of wearable computing device 100 of FIG. 43.

In some embodiments, strap 111, which fixes the HMD 110 on user 10, includes one or more capacitive electrodes 4300, for example, positioned adjacent a top of the head of user 10 and the back of the head of user 10, as shown in FIG. 43. Electrodes 4300 may be disposed in strap 111 of wearable computing device 100 to receive bio-signal data of user 10. In some embodiments, received bio-signal data may include brainwave data of user 10. In some embodiments, capacitive electrode 4300 may be a noncontact electrode that does not come into direct contact with skin 12 of user 10.

Strap 111 may include a compressible foam 4302 which may conform to the shape of the head of user 10. In some embodiments, compressible foam 4302 may be formed of an open cell foam, such as open cell foam material known to a user skilled in the art. Compressible foam 4302 may be compressible such that when the wearable computing device 100 is affixed to the head of user 10, compressible foam 4302 conforms to the head of user 10. In use, the compressible foam 4302 may be compressed and conform to the head of user 10 by clinching of strap 111 that secures HMD 110 to user 10.

In some embodiments, on a surface of compressible foam 4302 adjacent user's 10 head, a conductive layer 4304 of capacitive electrode 4300 is secured to compressible foam 4302.

Conductive layer 4304 may have a thickness between 1 and 100 µm, in an example 20 µm. Conductive layer 4304 may be formed of a conductive material such as a polymer substrate with conductive ink, a conductive polymer, conductive fabric or a flexible PCB.

Conductive layer 4304 may be insulated adjacent the head of user 10 with an insulating layer 4306. Insulating layer 4306 forms a dielectric medium, creating a capacitive coupling between conductive layer 4304 and skin 12 of user 10. In some embodiments, hair or other body tissue of user 10 may further contribute to the dielectric formed by insulating layer 4306 and the capacitive coupling may form across hair or other body tissue of user 10. Hair of user 10 may be compressed and held in place by the pressure exerted by compressible 4302.

Insulating layer 4306 may have a thickness between 1 and 100 µm, in an example 50 µm. Insulating layer 4306 may be formed of a polymer, for example, polyester.

Insulating layer 4306, by providing a minimal insulating layer between conductive layer 4304 and skin 12 of user 10, may moderate variability in the capacitive coupling between conductive layer 4304 and skin 12 of user 10 caused by variances in the properties of user's 10 hair. Insulating layer 4306 may also minimize salt bridging effects that may arise, for example, due to user 10 sweat creating a salt bridge forming an electrical connection between electrodes leading to improper readings being obtained by the electrodes.

In some embodiments, conductive layer 4304 may be connected to the HMD 110 or sensor electronics, for example, a signal conditioning and amplification circuit, via a wire (not shown).

In various implementations, the wearable device 100 may include a tracker or other sensors, input devices, and output devices. In some embodiments, for example, the tracker is an inertial sensor for measuring movement of the device 100. It detects the 3-dimensional coordinates of the wearable device 100 and accordingly its user's location, orientation or movement in the VR environment including the user's gaze direction. The tracker, for example, comprises one or more accelerometers and/or gyroscopes. The wearable device 100 may comprise a touch sensor for receiving touch input from the user and tactile device for providing vibrational and force feedback to the user. The wearable device 100 may further include input devices such as mouse, keyboard and joystick. In some embodiments, the wearable device 100 may be a training system.

Electrical signals may be measured on other regions of the head and may be mounted to the supporting architecture of the wearable device 100. Typically these are elasticized fabric. Sensors that measure scalp potentials would typically have a fingered design to allow the conductive electrodes to reach through the hair to reach the surface of the scalp. The fingers may be springy to allow for comfort and allow for the user to manipulate them in a fashion that will spread and disperse hair to facilitate a low impedance interface to skin of the scalp. Capacitive electrodes may also be used, for example, capacitive electrode 4300 as discussed above. Capacitive electrodes may provide for a slight air gap between the electrode and the scalp.

Many electrodes may be used if possible to allow for a higher dimensional bio-signal to facilitate denoising signal processing and to acquire more accurate spatial information of the bio-signal activity. Good spatial resolution may allow for more precise interpretation of the electrical activity in the brain as well as muscular activity in the face and head. This may allow for improved accuracy in estimating a user's cognitive or emotional state.

The wearable computing device 100 may be embodied, for example, as a wearable headset worn on a user's head. The wearable computing device may include a computing device, or connect to a computing device (not shown), and may be configured to create a VR environment on the HMD 110 and sound generator 1140 for presentation to a user; receive bio-signal data of the user from sensors such as electrode 130, optical device 140, electrode 149, eye tracker 150, breath sensor 160, electrode 170, non-contact electrode 180, sensors 192, bio-signal sensor 3500, bio-signal sensor 3700, capacitive electrode 4300, at least one of the bio-signal sensors comprising a brainwave sensor, and the received bio-signal data comprising at least brainwave data of the user; and determine brain state response elicited by the VR environment at least partly by determining a correspondence between the brainwave data and a predefined bio-signal measurement stored in a user profile, the predefined bio-signal measurement associated with predefined brain state response type. The brain state response may comprise an emotional response type. The wearable device 100 may be in the form of a virtual reality headset.

In some embodiments, the wearable computing device 100 includes an electronics module receiving bio-signals from sensors such as electrode 130, optical device 140, electrode 149, eye tracker 150, breath sensor 160, electrode 170, non-contact electrode 180, sensors 192, bio-signal sensor 3500, bio-signal sensor 3700, capacitive electrode 4300, or any combination thereof. In some embodiments, the module includes analog signal conditioning circuitry. In some embodiments, the electronics module includes a processor. In some embodiments, the module includes a wireless transmitter, such as a RF radio, for data transmission, or a wired connection connecting to the HMD 110 and/or the computing device. In some embodiments, the electronics module is the computing device.

Embodiments of the wearable computing device 100 may provide for the collection, analysis, and association of particular bio-signal and non-bio-signal data with specific brain states for both individual users and user groups. The collected data, analyzed data or functionality of the systems and methods may be shared with others, such as third party applications and other users. Connections between any of the computing devices, internal sensors (contained within the wearable device), external sensors (contained outside the wearable device), user effectors, and any servers may be encrypted. Collected and analyzed data may be used to build a user profile that is specific to a user.

The user profile data may be analyzed, such as by machine learning algorithms, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable device or other local computing device for providing feedback to the user, for example, to vibrate or provide some audio or visual indication to assist the user in achieving a particular mental state, such as a meditative state.

In use, the device may detect whether a user noticed a transient or moving stimulus in the visual or auditory field, and noticed characteristics of that stimulus encoded by the timecourse of the change, and using that information detected by the transient EEG response. This can be used, for example, to signal to an outside observer (e.g. a clinician, researcher, or other person not in the same VR environment) that the user has noticed or attended to the stimulus; to signal, via for example a change of facial expression on a virtual or holographic avatar, or a colour change of said avatar, to another observer in the VR environment that the user noticed or attended to said stimulus event; or to signal, via for example a change of facial expressions of multiple avatars, or via an event in a VR environment, which of multiple users in said VR environment noticed or attended to a stimulus event.

In some embodiments, the device may also detect a user's cognitive state based on a combination of continuous brainwave signal and transient brain responses to virtual stimulus events in the visual, auditory or tactile domain, in a VR environment, to predict thresholds for detection of subsequent virtual events in the auditory, visual, or tactile field, and to optimize the presentation of subsequent stimuli in said VR environment for detection or to change the likelihood of the stimulus being either consciously attended or not consciously attended.

In some embodiments, the device may actively adapt the rate of stimulus presentation based on a combination of continuous brainwave signal and transient brain responses to virtual stimulus events in the visual, auditory or tactile domain, in a VR environment.

In some embodiments, the device may accept inputs from a head- or body-worn continuous visual recognizer, such as a camera and computer/software system which recognizes objects, scenes, or actions in the user's visual or auditory field, combines that information with brainwave information time-synchronized to the visual field events via a computer, and uses the combined information to determine whether the user noticed the object, scene, or action, attended to the object, scene, or action, or whether the user recognized the object, scene, or action.

In some embodiments, the system accepts inputs from a head- or body-worn continuous auditory recognizer, such as a camera and computer/software system which recognizes objects, scenes, or actions in the user's auditory or auditory field, combines that information with brainwave information time-synchronized to the auditory field events via a computer, and uses the combined information to determine whether the user noticed the object, scene, or action, attended to the object, scene, or action, or whether the user recognized the object, scene, or action.

In some embodiments, the system accepts inputs from a head- or body-worn continuous visual recognizer, such as a camera and computer/software system which recognizes human faces in the user's visual or auditory field, combines that information with brainwave information time-synchronized to the visual field events via a computer, and uses the combined information to determine whether the user recognized the face.

In some embodiments, the visual or auditory recognizer is not worn by the user, but by another user, or is a stationary or object mounted recognizer system. In some embodiments, electrodes on the face or forehead may measure muscle activity associated with facial expression of emotions (for example: frown, surprise, puzzlement, sadness, happiness) in which the user's brainwaves are combined with bio-signal information about emotional facial expression to produce a change in state of a user's avatar in said VR environment.

In some embodiments, the diminution of a user's evoked brain response to a visual or auditory event in the VR environment (as in habituation or learning) after repeated stimulus presentations may be used to predict how frequently a new stimulus of a certain type should be presented to the user to achieve familiarity—as in, for example, a memorization task, or a recognition task—and can be used to adapt an environment to optimize engagement, or the retention of information.

In some embodiments, the diminution of a user's evoked brain response to a visual or auditory event in the VR environment (as in habituation or learning) after repeated stimulus presentations may be used to predict how frequently a new stimulus of a certain type should be presented to the user to maintain a specific state of vigilance or responsiveness, or of interest. For example, a system designed to use brain response information within a VR environment, which determines a user's likelihood of loss of engagement or boredom, and adapts the environment continuously to maximize engagement.

In some embodiments, a profile of the user including the user's brain response and engagement may be determined within the user's first few minutes within a VR environment, and the environment is adapted to a threshold of interactivity to maintain engagement without continuously monitoring the user's brain response.

In some embodiments, multiple users in a VR environment, in which one or more lead user (for example an instructor) is presented with information overlaid on another user's virtual space, or another user's avatar, may allow the lead user to determine which of the other users (for example students) attended to or were engaged with specific aspects of information presented (for example, lesson elements) in the VR environment, based on the other users' individual brain responses synchronized to the presentation of said information events. For example, in a virtual classroom, or in a physical classroom with mixed reality, a virtual display or information about what taught material each student is likely to have retained.

In some embodiments, the content is presented in the physical environment.

User State Visualization

As an illustrative example, the VR environment may present information about a user's state. The wearable device processes user bio-signal data and provides feedback through at least one feedback module. Feedback in the VR environment may provide a more intuitive understanding for the user's state than a regular display.

Figure 31:
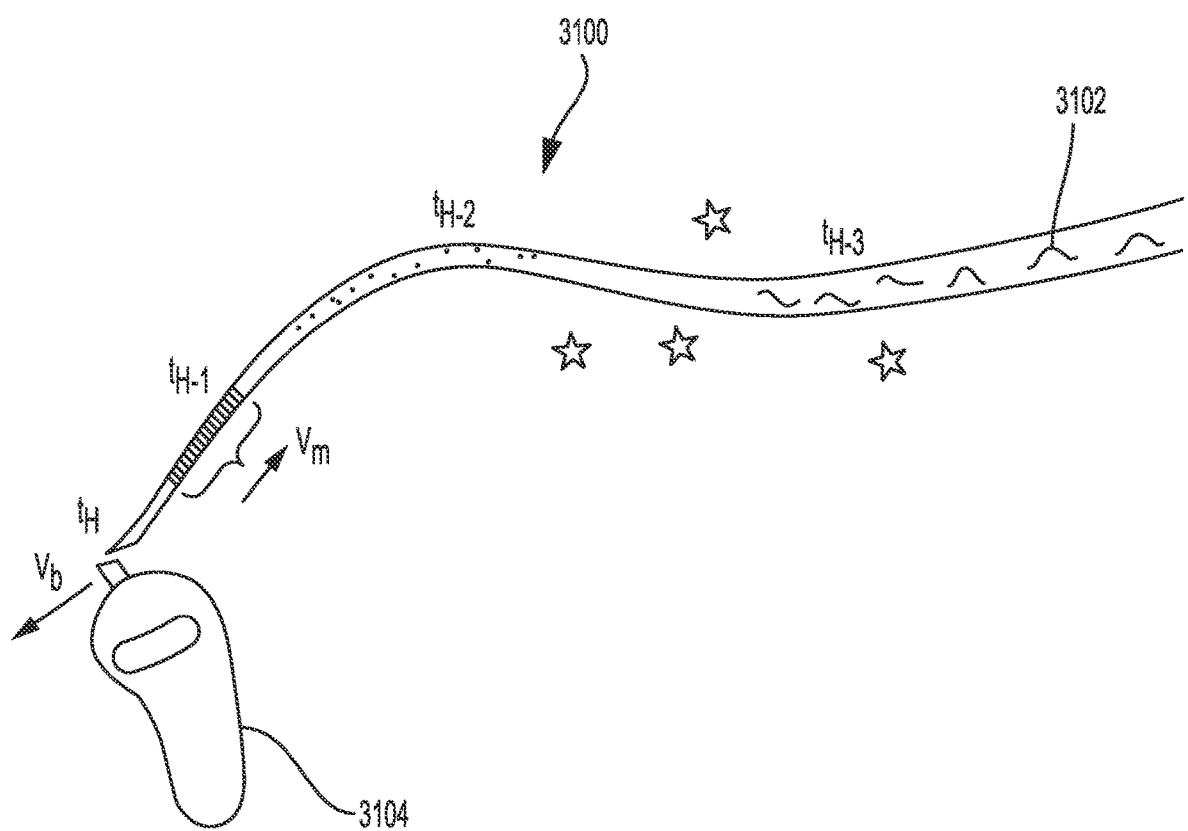
FIG. 31 illustrates a schematic representation of a memory trace, according to an embodiment.

In one example, and having reference to FIG. 31, the user state visualization includes a memory trace 3100. In some embodiments, at least one object 3102 is created and projected in the VR environment. For example, as a user moves in a first direction, the user may leave at least one object indicative of the user state. Alternatively, the at least one object indicative of the user state is projected from a source and radiates in a propagation direction. For example, the at least one object 3102 is a continuous trail or a series of discrete objects indicative of the user state. The at least one object 3102 is like a bread crumb trail of the user state. For example, as shown in FIG. 31, objects 3102 are represented at current time $t_H$, at time $t_{H-1}$, at time $t_{H-2}$, and at time $t_{H-3}$. In this manner, the feeling of time is made accessible to the user. In some embodiments, the origin of the trace moves at a velocity in the first direction, $V_b$, based on the movement of the user, or a manual user input, such as a controller 3104 or other device, represented in the VR environment. In some embodiments, the elements of visual stimulus within a section of the trace propagate in a second direction at a velocity $V_m$, such as being represented as a standing wave or moving sparkles. In some embodiments, for example, the trace represents linear time, and the elements moving at $V_m$ represent a mental state within linear time. In changing the rate at which the at least one object is generated, the perception of time can be altered. In some embodiments, user state can be used to affect the rate at which the last one object is projected in the VR environment. In this manner, a feedback loop may be created that can help a user enter different states of consciousness.

Figure 32:
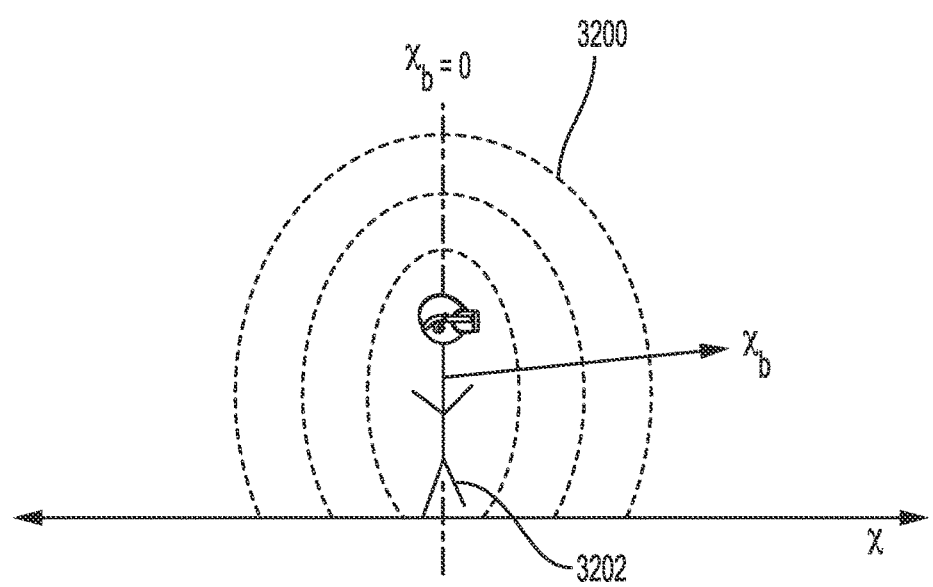
FIG. 32 illustrates a schematic representation of a breath envelope, according to an embodiment.

In another example, and having reference to FIG. 32, the user state visualization includes a breath envelope 3200. In some embodiments, the breath envelope is presented as a field surrounding the user's body 3202 in the VR environment. The density of the field decays as distance, for example, as indicated by $x_b$ in the x-axis in FIG. 32, increases from the user. The size and density of the field is affected by the state of the user's breathing (such as breathing rate or a duration of a breath) and body oxygen content. In some embodiments, the bio-signal sensor used to detect breathing is a breath sensor, for example, breath sensor 160. In some embodiments, breathing is detected using a stretchable strap worn on a user's chest (optionally including ECG or PPG functionality), accelerometers, gyroscopic sensors, or a combination thereof. In some embodiments, the bio-signal sensor used to detect the body oxygen content includes a pulse oximetry sensor.

In some embodiments, the field is larger when the user has more air in their lungs. In some embodiments, the field is more dense when the user has more oxygen in their body. The field is used to affect a parameter of an object within the user's field to create a feeling of connection between the breath and the user's immediate vicinity in the VR environment. In some embodiments, a denser field has a stronger effect on the parameter of the object. In some embodiments, the parameter is a dimension or other behavior of the object. For example, if the user breathes heavily for a period of time and increases the amount of oxygen in the body, the field can be used to distort the shape of objects, such as making them larger within the acting range of the breath envelope. In some embodiments, the more oxygenated the user becomes, objects within the breath envelope would be enlarged in the VR environment. Similarly, in some embodiments, sound may also be affected in a similar way. An object having a sound associated therewith may be modulated such that a sound emitted by the sound generator and associated with the object may become louder or softer or change in spectral distribution within the breath envelope field. In some embodiments, the breath envelope is displayed in the VR environment as an object.

Figure 33:
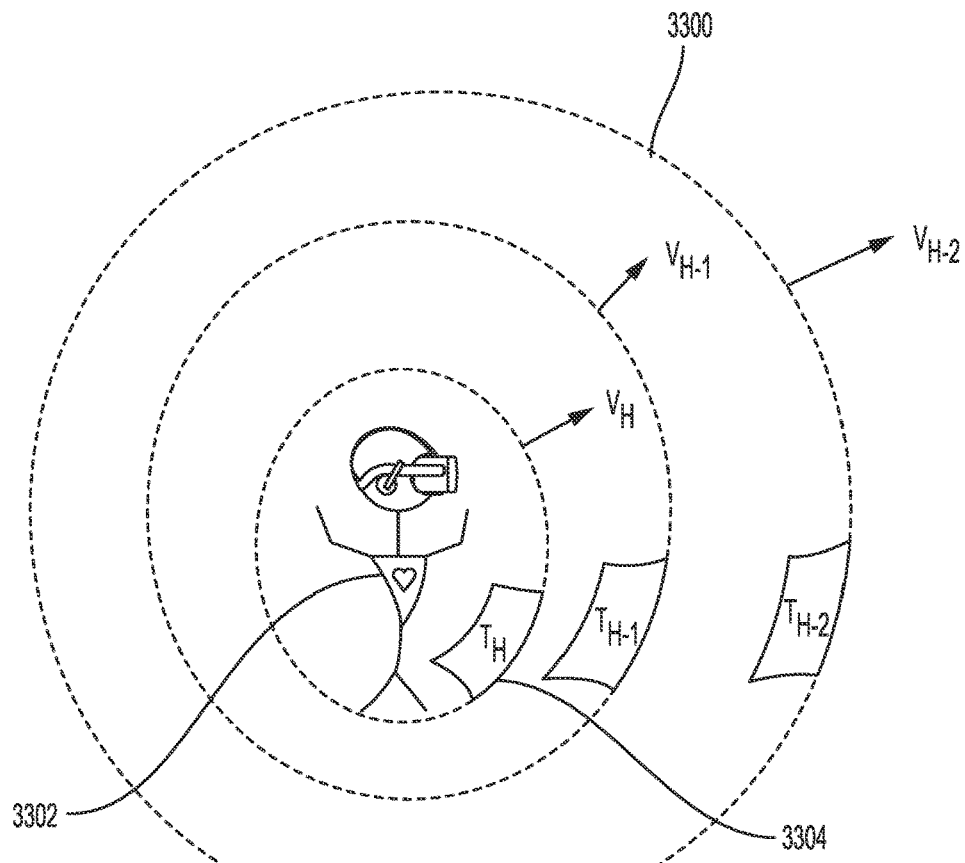
FIG. 33 illustrates a schematic representation of a heart-wave manifold, according to an embodiment.

In another example, and having reference to FIG. 33, the user state visualization includes a heartwave manifold 3300. In some embodiments, the heartwave manifold 3300 is a field that radiates outward from the user's virtual heart 3302. In some embodiments, the heartwave manifold 3300 is synchronized with the user's heart. In some embodiments, the heartwave manifold 3300 is shaped as a sphere or ellipsoid. In some embodiments, the field includes at least one object 3304 in the VR environment directly visible to the user. In some embodiments, the at least one object 3304 includes a series of spheres, shown in part in FIG. 33 as $T_H$, $T_{H-1}$ and $T_{H-2}$, growing and propagating outward radially, for example, at velocities $V_H$, $V_{H-1}$ and $V_{H-2}$ as shown in FIG. 33, with the passage of time. In some embodiments, a new object is created on each heartbeat. In some embodiments, each new object propagates away from the origin point. In such manner, the objects form a 3D ripple according to the heartbeats of the user. In some embodiments, the field is not directly visible in the VR environment. In some embodiments, the field is interactive with the VR environment, giving the user indirect feedback from the user's heart. In some embodiments where the field is directly visible in the VR environment, the heartwave manifold includes information of the user's mind/body state associated therewith, allowing it to display the user's state information recorded at that instant of time or vary in accordance with the ongoing variation in the mind/body state. These patterns displayed on the heartwaves manifolds may change as they propagate outward in the VR environment.

In some embodiments where the field is directly visible in the VR environment, the user's brain state is rendered onto the at least one object of the heartwave manifold. In some embodiments, as the at least one object of the heartwave manifold expands, the rendered spatial pattern may be associated with the depth in the brain from where the activity is associated. For example, when one object of the at least one object of the heartwave manifold is first created, the user sees deep brain activity. As the object propagates outward, the user sees activity at shallower depths of the brain. Eventually, the user sees surface activity of the brain. In some embodiments, information could be integrated from various sensors to represent a standard brain model, or customized to a user's fMRI-based brain model. In some embodiments, the rendered spatial pattern is associated with the position, from front-to-back, of the brain, starting with the front of the frontal lobe to the rear of the occipital lobe. In some embodiments, the rendered spatial pattern is associated with the position, from starting from a midline and moves outward. In some embodiments, the rendered spatial pattern is associated with activity at different frequencies of a user's brainwave state. For example, when one object of the at least one object of the heartwave manifold is first created, the user sees their brain's theta wave activity. As the object propagates outward, the user sees the activity of their brain at higher frequencies. Eventually, the user sees their brain's gamma wave activity.

In some embodiments, the expansion of the at least one object is based on time such that the mind/body state is less defined or visible as the at least one object expands outward. In some embodiments, the significance of the user's state at the time the at least one object was generated affects the decay rate. For example, heartwave associated with a surprising event or strong emotional state may be visible for longer. Such surprising event or emotional state may be associated with an ERP, heart rate variability, skin galvanometry, anomalous movements (such as jerks, jumps, or microexpressions), or a combination thereof.

In some embodiments, the at least one object surface may be dynamically rendered based on the user's mind/body state in real time so that the rendered surface reflects the user's current mind/body state. This may facilitate connection with other users in the VR environment. These users may be physically proximate, or remote from one another. In embodiments where the users are remote from one another, the users may be connected to one or more computers for processing information in the VR environment via a computer network.

In some embodiments, information associated with the heartwave may change over time as more time synchronized information becomes available. For example, if considering the action of a first user's heart related to second user, the feedback loop is slowed by computer and communication lag, as well as brain associated perceptual lag. Information of the second user's heart reacting to the first user's heart would be available at some later time than the first user's heartbeat. When this information becomes available, the dynamic texture associated with the at least one object of the heartwave manifold of the first user would change to reveal the relationship. This exemplary interaction allows the users to see heart based connection between them, as well as the transition between heart reactivity to heart coherence.

For example, ECG data and heart sensor data may be processed and displayed in the VR environment such that a heartbeat is presented as a sphere. A property of the sphere, such as the size or color, may be modified as the heartbeat changes. In some embodiments, the size may be dependent on the heart rate. For example, as a user's heart rate increases, the sphere can grow in size, or go from a resting state color (e.g. green) to a exertion state color (e.g. red). Such integrated information may be more accurate in estimating a user's state than continuous EEG alone.

Figure 34:
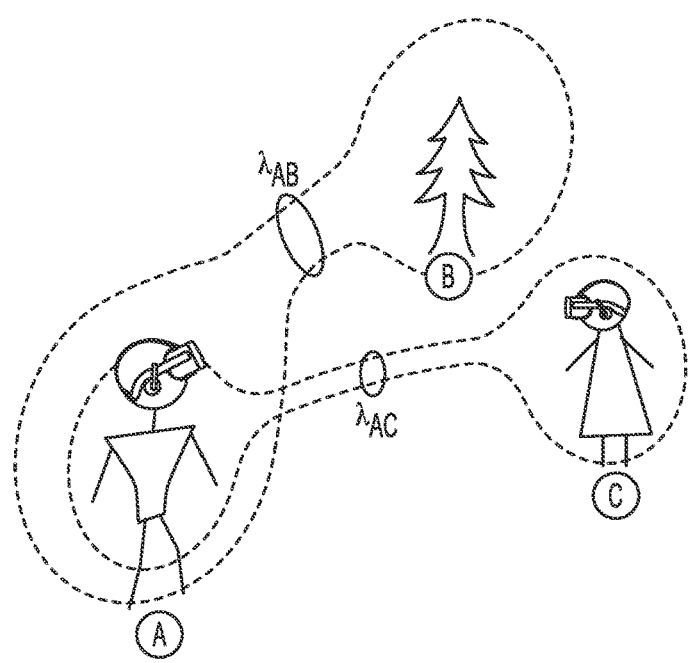
FIG. 34 illustrates a schematic representation of an objectification field, according to an embodiment.

In another example, and having reference to FIG. 34, the user state visualization includes an objectification field associated with the level of connection a user has with an object or another user in the environment. The objectification field may be displayed in the VR environment, showing the connectivity to the user or other users, or it may be used to affect the environment or other users (such as through visual or tactile feedback provided to the other user) who are within or proximal to the field. For example, where an object is a non-player character ("NPC"), the position of the eyes of the NPC may be modified in accordance with the objectification field. For example, the NPC's gaze is modified to be aligned with a local objectification field. The field strength is directional and is associated with the user's interest level in another actor. In some embodiments, the user's interest in another actor is determined based on ERP. The user's brain is determined to be responsive to events involving the other user, relative to that user's baseline responsiveness to novel and familiar stimuli. As such, the objectification field is not always equal between two users. For example, user A's interest in user C, $A_A c$, may be different than user C's interest in user A, $\lambda_{CA}$. In the case of an object B, the field of user A's interest in user B, $\lambda_{AB}$, may be simple, for example decaying with distance or visibility. For complex relationships, such as between two users A and C, $\lambda_{AC}$ and $\lambda_{CA}$ can be used to calculate mutual interest. For example, the mutual interest is the product of $\lambda_{AC}$ and $\lambda_{CA}$. The mutual interest optionally includes a coherence term indicating that the users are on the same wavelength. In some embodiments, the coherence term is computed using the level of synchrony between the two users' time varying state feature vectors. For example, one type of synchrony includes the spectral coherence between two users' brainwaves who are proximal to each other in the VR environment. Synchrony between a user and an NPC or other non-user object is also possible. For example, this may be computed based on variance of the time varying distance between the location of the user and the NPC or the non-user object in the VR environment. In some embodiments, the VR environment is a game where a user dances with another user or an NPC and scoring is based on the synchrony of their movements.

User State Painting

In another exemplary application of the wearable computing device, the VR environment is a 3D painting application. The 3D painting application may be similar to Tilt Brush™ from Google. In Tilt Brush™, a user (i.e. artist) is able to paint in multiple dimensions according to the positioning of a controller. A brush stroke applied is an object in the VR environment. By incorporating the artists brainwave state, the colors may change based on the brain state of the individual. The brainwave state can dynamically determine the color that the brush will output. In this manner, a parameter of object (e.g. the color of a particular portion of a brush stroke) in the VR environment is dynamically altered depending on the brainwave state of the user during the creation of the object. Alternatively, a brush stroke applied by a user may constantly change depending on the brainwave state of the user. In this manner, a parameter of object (e.g. the color of a particular portion of a brush stroke) in the VR environment is dynamically altered depending on the brainwave state of the user after the creation of the object. By modifying the color according to the brainwave state of the user, a more direct emotional response can be output onto the virtual canvas. In contrast, in a traditional, physical medium, the color of the brush cannot be adjusted dynamically. By the time the artist mixes a color according to their emotional state, the artist's emotional state may have shifted and a new color may need to be mixed in order to reflect the new state. Further, the paint applied by the brush is not dynamically altered during a single stroke; in order to change the color on the canvas, the new color of paint must be applied to the brush and a new stroke begun.

Meditation

In another exemplary application of the wearable computing device, the VR environment is a meditation application. While meditation can be felt, it can be hard to quantify in a way that other people can understand. It can also be easy for people doing meditation to feel as though they have slipped behind or are not making enough progress. This creates a distraction that is anathema to the act of meditation itself. Embodiments described herein may allow people who are meditating to see their progress as feedback. This can be helpful for people who have been asked to meditate as part of cognitive behavioural therapy, or to bring down blood pressure, or manage chronic pain.

For example, the user may want to participate in a meditation program at a crowded/noisy/non-conducive setting. To overcome this environmental obstacle, the user dons a pair of VR goggles. The goggles provide a virtual meditation environment in which the area surrounding the user is free of distractions. This VR environment can be mapped using a device which contains sensors for mapping a 3D environment. The user can participate in either a walking or a sitting meditation practice with the distracting elements of the setting blocked out. As the user practices meditation, their EEG state is being monitored. The user can visualize their EEG state during the meditation practice; it can be presented like a music visualizer—a series of peaks and troughs can become visible travelling towards them, corresponding to their mental state. Alternatively, their EEG state can modify the VR environment itself. For example, the 3D environment can be a beach with the EEG state being represented visually and/or aurally by waves washing to the shore. The VR environment may be further modified by other user state data. For example, a user's heart rate can be represented by the clouds in the sky. This can allow the user to see and hear how their meditation is progressing, i.e. whether they are meeting their meditation goals in terms of relaxation, etc. The user can then optimize their meditation practice to meet specific goals by modifying their breathing or some other variables to create a different outcome during the meditation practice.

Embodiments described herein translates EEG data, heart rate and pulse detection, and eye-tracking to generate feedback outputs like real time dynamic changes to the VR environment (such as a change in music or ambient sound, or shifts in light, transparency, or opacity, or topography), while also creating data for reports that wearers could opt into or share with friends and supporters.

According to an aspect, there is provided a system for detecting a user's notice to a transient or moving stimulus in the user's visual or auditory field in a virtual or mixed environment, and to characteristics of that stimulus encoded by the timecourse of the change, and using the information detected by a transient EEG response for: signalling to an outside observer (a clinician, researcher, or other person not in the same virtual or mixed reality environment) that the user has noticed or attended to the stimulus; signalling, to another observer in the virtual or mixed environment, that the user noticed or attended to said stimulus event; or signalling, via for example a change of facial expressions of multiple avatars, or via an event in a virtual environment, which of multiple users in said virtual or mixed reality environment noticed or attended to a stimulus event.

In some embodiments, the signalling to another observer is effected via a change of facial expression on a virtual or holographic avatar, or a colour change of said avatar.

According to an aspect, there is provided a system for detecting a user's cognitive state based on a combination of continuous brainwave signal and transient brain responses to virtual stimulus events in a visual, auditory or tactile domain, in a virtual, augmented or mixed reality environment, to predict thresholds for the user's detection of subsequent virtual events in the auditory, visual, or tactile field, and to optimize the presentation of subsequent stimuli in said virtual, augmented or mixed reality environment for detection or to change the likelihood of the stimulus being either consciously attended or not consciously attended.

According to an aspect, there is provided a system for actively adapting a rate of stimulus presentation based on a combination of continuous brainwave signal and transient brain responses to virtual stimulus events in the visual, auditory or tactile domain, in a virtual, augmented or mixed reality environment.

According to an aspect, there is provided a system which accepts inputs from a head- or body-worn continuous visual recognizer, such as a camera and computer/software system which recognizes objects, scenes, or actions in the user's visual or auditory field, combines that information with brainwave information time-synchronized to the visual field events via a computer, and uses the combined information to determine whether the user noticed the object, scene, or action, attended to the object, scene, or action, or whether the user recognized the object, scene, or action.

According to an aspect, there is provided a system which accepts inputs from a head- or body-worn continuous auditory recognizer, such as a camera and computer/software system which recognizes objects, scenes, or actions in the user's auditory or auditory field, combines that information with brainwave information time-synchronized to the auditory field events via a computer, and uses the combined information to determine whether the user noticed the object, scene, or action, attended to the object, scene, or action, or whether the user recognized the object, scene, or action.

According to an aspect, there is provided a system which accepts inputs from a head- or body-worn continuous visual recognizer, such as a camera and computer/software system which recognizes human faces in the user's visual or auditory field, combines that information with brainwave information time-synchronized to the visual field events via a computer, and uses the combined information to determine whether the user recognized the face.

In some embodiments, the visual or auditory recognizer is not worn by the user but worn by another person, or being a stationary or object mounted recognizer system.

In some embodiments, the system further comprises an additional input of electrodes on the face or forehead to measure muscle activity associated with facial expression of emotion in which the user's brainwaves are combined with bio-signal information about emotional facial expression to produce a change in state of a user's avatar in said virtual environment.

In some embodiments, the emotion includes frown, surprise, puzzlement, sadness, or happiness.

In some embodiments, the diminution of a user's evoked brain response to a visual or auditory event in the virtual environment (as in habituation or learning) after repeated stimulus presentations is used to predict how frequently a new stimulus of a certain type should be presented to the user to achieve familiarity.

In some embodiments, the new stimulus includes a memorization task, or a recognition task.

In some embodiments, the diminution of the user's evoked brain response is used to adapt an environment to optimize engagement, or the retention of information.

In some embodiments, the diminution of a user's evoked brain response to a visual or auditory event in the virtual environment (as in habituation or learning) after repeated stimulus presentations is used to predict how frequently a new stimulus of a certain type should be presented to the user to maintain a specific state of vigilance or responsiveness, or of interest.

In some embodiments, the system uses brain response information within a virtual or mixed reality environment, which determines a user's likelihood of loss of engagement or boredom, and adapts the environment continuously to maximize engagement.

In some embodiments, a user's brain response and engagement is determined quickly, within the user's first few minutes within the virtual or mixed reality environment, and the environment is adapted to a set point level of richness to maintain optimal engagement without continuously monitoring the user's brain response.

In some embodiments, there are multiple users in a virtual or mixed reality environment, in which one or more lead user (for example an instructor) is presented with information overlaid on a user's virtual space, or a user's avatar, to allow the lead user to determine which other users (for example students) attended to or were engaged with specific aspects of information presented (for example, lesson elements) in the virtual or mixed reality environment, based on the other users' individual brain responses synchronized to the presentation of said information events.

In some embodiments, the environment is a virtual classroom, or a physical classroom with mixed reality, a virtual display or information about what taught material each student is likely to have retained.

In some embodiments, content is presented in the physical environment.

Figure 45:
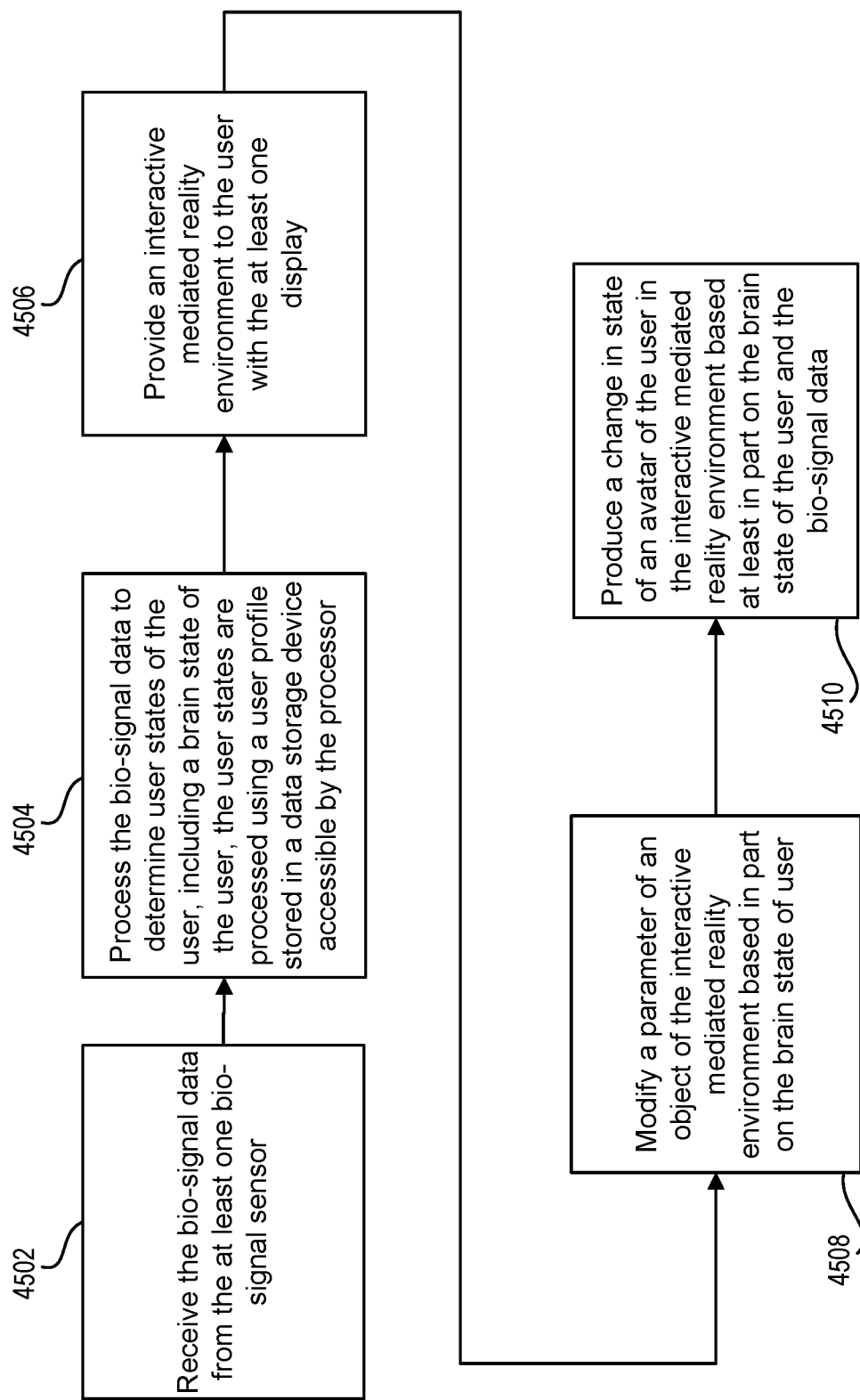
FIG. 45 illustrates a flow chart of an example process diagram, according to an embodiment.

According to an aspect, there is provided a system, apparatus, device, process, or method including one or more features as set out in the description, claims, drawings, or any combination thereof. FIG. 45 illustrates a flow chart of an example process diagram, according to an embodiment. In some embodiments, the system is configured to receive the bio-signal data from the at least one bio-signal sensor (4502), process the bio-signal data to determine user states of the user, including a brain state of the user, the user states are processed using a user profile stored in a data storage device accessible by the processor (4504), provide an interactive mediated reality environment to the user with the at least one display (4506), modify a parameter of an object of the interactive mediated reality environment based in part on the brain state of user (4508), and produce a change in state of an avatar of the user in the interactive mediated reality environment based at least in part on the brain state of the user and the bio-signal data (4510).

General

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:

1. A mediated reality system comprising:
a wearable device comprising at least one bio-signal sensor receiving bio-signal data from a user; wherein the at least one bio-signal sensor comprises a brainwave sensor;
at least one display; and
a processor configured to:
receive the bio-signal data from the at least one bio-signal sensor;
process the bio-signal data to determine user states of the user, including a brain state of the user, the user states are processed using a user profile stored in a data storage device accessible by the processor;
provide an interactive mediated reality environment to the user with the at least one display; modify a parameter of an object of the interactive mediated reality environment based in part on the brain state of user; and
produce a change in state of an avatar of the user in the interactive mediated reality environment based at least in part on the brain state of the user and the bio-signal data.

2. The mediated reality system of claim 1 wherein:
the user states comprise at least one of cognitive state and emotional state.

3. The mediated reality system of claim 1 further comprising:
a camera configured to detect a physical environment of the user; and
wherein the processor is configured to modify the interactive mediated reality environment based in part on the physical environment of the user.

4. The mediated reality system of claim 1 further comprising:
effectors in a physical environment of the user; and
wherein the processor is configured to instruct the effectors to modify the physical environment of the user based in part on the interactive mediated reality environment of the user.

5. The mediated reality system of claim 1 further comprising:
an eye tracker configured to track a gaze of the user; and
wherein the processor is configured to modify the avatar based in part on the gaze of the user.

6. The mediated reality system of claim 1 further comprising:
a breath sensor configured to detect breath data of the user; and
wherein the processor is configured to modify the avatar based in part on the breath data of the user.

7. The mediated reality system of claim 1 further comprising:
at least one sensor configured to detect muscle activity of the user to determine facial expressions of the user; and
wherein the processor is configured to modify the avatar based in part on the facial expressions of the user.

8. The mediated reality system of claim 1 wherein:
the at least one bio-signal sensor comprises at least one of an EEG sensor, a galvanometer sensor, an electrocardiograph sensor, a heart rate sensor, an eye-tracking sensor, a blood pressure sensor, a pedometer, a gyroscope, and an EOG sensor.

9. The mediated reality system of claim 1 wherein:
the user can generate an object in the interactive mediated reality environment; and
at least one characteristic of the object is based in part on the brain state of the user.

10. The mediated reality system of claim 9 wherein:
the at least one characteristic of the object is persistence of the object in the interactive mediated reality environment.

11. The mediated reality system of claim 1 wherein:
the system is configured to communicate the brain state of the user with an outside party.

12. The mediated reality system of claim 1 wherein:
the processor is configured to generate a field that radiates outward from the avatar of the user based in part on a bio-signal data; and the field is interactive with the interactive mediated reality environment.

13. The mediated reality system of claim 1 wherein:

the bio-signal sensor comprises:
- a body,
- an electrode extendable into the body,
- the electrode having a contact end configured to receive an electrical bio-signal from skin of the user,
- wherein in response to a downward force acting on the bio-signal sensor to urge the bio-signal sensor against the skin of the user and upon contact with the skin of the user,
- the electrode is configured for movement into the body along a movement axis,
- an actuator attached to the body and operatively connected to the electrode urging the electrode out of the body along the movement axis toward an extended position, and
- a contact adjuster connected to the electrode,
- the contact adjuster comprising a handle manipulatable by the user to reduce noise the electrical bio-signal caused by impedance of the user's hair.

14. The mediated reality system of claim 1 wherein:
the wearable device comprises at least one securement strap to secure the wearable device to the user;
a surface of the at least one securement strap is configured to contact skin of the user; and
the surface comprises at least one embedded sensor.

15. The mediated reality system of claim 1 wherein:
the wearable device comprises the at least one display; and
the display comprises a head mounted display.

16. The mediated reality system of claim 15 wherein:
the wearable device comprises a display isolator to reduce visual stimuli from sources other than the display;
a surface of the display isolator Is configured to contact a face of the user; and
the surface comprises at least one embedded sensor.

17. The mediated reality system of claim 16 wherein:
the at least one embedded sensor comprises at least one of a pressure sensor and a strain sensor to measure face movement.

18. The mediated reality system of claim 16 wherein:
the at least one embedded sensor is located proximate to an eye of the user to detect muscle movements around the eye of the user.

19. The mediated reality system of claim 1 further comprising:
one or more other users participating in the interactive mediated reality environment; and
wherein the at least one aspect of the interactive mediated reality environment is modified based in part on one or more brain states of the one or more other users.

20. The mediated reality system of claim 19 wherein:
the processor provides the interactive mediated reality environment with a user state visualization having an objectification field associated with the level of connection the user has with an object or another user in the environment by computing mutual interest based on a coherence term.

* * * * *